(12) United States Patent
Carniaux et al.

(10) Patent No.: US 8,697,876 B2
(45) Date of Patent: Apr. 15, 2014

(54) COMPOSITIONS AND METHODS OF SYNTHESIS OF PYRIDINOLYPIPERIDINE 5-HT1F AGONISTS

(75) Inventors: Jean-Francois Carniaux, Abingdon (GB); Jonathan Cummins, Didcot (GB)

(73) Assignee: Colucid Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 13/637,566

(22) PCT Filed: Mar. 31, 2011

(86) PCT No.: PCT/US2011/030740
§ 371 (c)(1),
(2), (4) Date: Dec. 4, 2012

(87) PCT Pub. No.: WO2011/123654
PCT Pub. Date: Oct. 6, 2011

(65) Prior Publication Data
US 2013/0072524 A1    Mar. 21, 2013

Related U.S. Application Data

(60) Provisional application No. 61/320,517, filed on Apr. 2, 2010.

(51) Int. Cl.
*C07D 401/06* (2006.01)

(52) U.S. Cl.
USPC .................................................. 546/194

(58) Field of Classification Search
None
See application file for complete search history.

(56) References Cited

U.S. PATENT DOCUMENTS

| | | | |
|---|---|---|---|
| 5,011,472 A | 4/1991 | Aebischer et al. |
| 5,023,252 A | 6/1991 | Hseih |
| 5,385,912 A | 1/1995 | Neuenschwander et al. |
| 5,521,196 A | 5/1996 | Audia et al. |
| 5,521,197 A | 5/1996 | Audia |
| 5,698,571 A | 12/1997 | Audia et al. |
| 5,708,008 A | 1/1998 | Audia et al. |
| 5,708,187 A | 1/1998 | Flaugh et al. |
| 5,721,252 A | 2/1998 | Audia et al. |
| 5,814,653 A | 9/1998 | Flaugh et al. |
| 5,817,671 A | 10/1998 | Filla et al. |
| 6,528,529 B1 | 3/2003 | Brann et al. |
| 6,650,463 B2 | 11/2003 | Obikawa et al. |
| 6,777,428 B1 | 8/2004 | Krushinski, Jr. et al. |
| 7,291,632 B2 | 11/2007 | Blanco-Pillado et al. |
| 7,423,050 B2 | 9/2008 | Cohen et al. |
| 7,608,629 B2 | 10/2009 | Blanco-Pillado et al. |
| 2002/0175891 A1 | 11/2002 | Obikawa et al. |
| 2003/0144285 A1 | 7/2003 | Brann et al. |
| 2003/0175445 A1 | 9/2003 | Kirsch et al. |
| 2005/0009871 A1 | 1/2005 | Ramesh et al. |
| 2005/0080112 A1 | 4/2005 | Madsen et al. |
| 2006/0211734 A1 | 9/2006 | Blanco-Pillado et al. |
| 2007/0129354 A1 | 6/2007 | Aston et al. |
| 2007/0219187 A1 | 9/2007 | Bessis et al. |
| 2007/0299110 A1 | 12/2007 | Gagliardi et al. |
| 2008/0300407 A1 | 12/2008 | Cohen et al. |
| 2010/0256187 A1 | 10/2010 | Pilgrim et al. |
| 2012/0329820 A1 | 12/2012 | Cohen et al. |

FOREIGN PATENT DOCUMENTS

| | | |
|---|---|---|
| JP | 03255426 A | 11/1991 |
| KR | 20060067738 A | 6/2006 |
| WO | WO-9314201 A1 | 7/1993 |
| WO | WO-9629075 A1 | 9/1996 |
| WO | WO-9713512 A1 | 4/1997 |
| WO | WO-9808502 A1 | 3/1998 |
| WO | WO-9815545 A1 | 4/1998 |
| WO | WO-9820875 A1 | 5/1998 |
| WO | WO-9846570 A1 | 10/1998 |
| WO | WO-9855115 A1 | 12/1998 |
| WO | WO-9925348 A1 | 5/1999 |
| WO | WO-0000487 A1 | 1/2000 |
| WO | WO-0000490 A2 | 1/2000 |
| WO | WO-0034266 A1 | 6/2000 |
| WO | WO-0047559 A2 | 8/2000 |
| WO | WO-0050426 A2 | 8/2000 |
| WO | WO-0105763 A2 | 1/2001 |
| WO | WO-0206196 A1 | 1/2002 |
| WO | WO-03000245 A1 | 1/2003 |
| WO | WO-03084949 A1 | 10/2003 |

(Continued)

OTHER PUBLICATIONS

Caira, "Crystalline Polymorphism of Organic Compounds," Topics in Current Chemistry, Springer, Berlin, DE, vol. 198, Jan. 1, 1998, pp. 163-208.

(Continued)

*Primary Examiner* — Janet L Anders
*Assistant Examiner* — Timothy R. Rozof
(74) *Attorney, Agent, or Firm* — Mintz Levin Cohn Ferris Glovsky and Popeo, P.C.; Ivor R. Elrifi; Heidi A. Erlacher

(57) ABSTRACT

The present invention provides a novel polymorph of the hemisuccinate salt of 2,4,6-trifluoro-N-[6-(1-methyl-piperidine-4-carbonyl)-pyridin-2-yl]-benzamide (Form A) characterized by a unique X-ray diffraction pattern and Differential Scanning Calorimetry profile, as well as a unique crystalline structure. This polymorph is useful in pharmaceutical compositions, for example, for the treatment and prevention of migraine. The invention also provides a process for the synthesis of pyridinoylpiperidine compounds of Formula I in high yield and high purity. In particular, the provides a process for the preparation of 2,4,6-trifluoro-N-[6-(1-methyl-piperidine-4-carbonyl)-pyridin-2-yl]-benzamide, its hemisuccinate salt and polymorph (Form A).

7 Claims, 13 Drawing Sheets

(56) References Cited

FOREIGN PATENT DOCUMENTS

| | | |
|---|---|---|
| WO | WO-2004047739 A2 | 6/2004 |
| WO | WO-2004089874 A1 | 10/2004 |
| WO | WO-2004099127 A1 | 11/2004 |
| WO | WO-2005007621 A2 | 1/2005 |
| WO | WO-2005044797 A1 | 5/2005 |
| WO | WO-2006048771 A1 | 5/2006 |
| WO | WO-2006058905 A1 | 6/2006 |
| WO | WO-2006081127 A2 | 8/2006 |
| WO | WO-2006108487 A1 | 10/2006 |
| WO | WO-2008114971 A1 | 9/2008 |
| WO | WO-2011123654 A1 | 10/2011 |

OTHER PUBLICATIONS

"A Placebo-Controlled Adaptive Treatment Assignment Study of Intravenous COL-144 in the Acute Treatment of Migraine." ClinicalTrials.gov Dec. 4, 2008. Web. Jun. 8, 2010. http://clinicaltrials.gov/ct2/show/NCT00384774?spons=Colucid&rank=2.

"Dose-ranging Study of Oral COL-144 in Acute Migraine Treatment—Study 1 of 2 for search of: Colucid", Clinical Trials, Apr. 16, 2009 (5 pages).

Adham et al. "Cloning of Another Human Serotonin Receptor (5-HT$_{1F}$): A Fifth 5-HT$_1$ Receptor Subtype Coupled to the Inhibition of Adenylate Cyclase." *PNAS*. 90(1993):408-412.

Berge et al. "Pharmaceutical Salts." *J. Pharm. Sci.* 66.1(1977):1-19.

Diener et al. "The Importance of Placebo in Headache Research." *Cephalalgia*. 28.10(2008):1003-1011.

Ferrari et al. "Oral Triptans (Serotonin 5-HT1B/1D Agonists) in Acute Migraine Treatment: A Meta-Analysis of 53 Trials." *Lancet*. 358(2001):1668-1675.

Goadsby et al. "Migraine—Current Understanding and Treatment." *N. Engl. J. Med*. 346.4(2002):257-270.

Goldstein et al. "Selective Seratonin 1F (5-HT1F) Receptor Agonist LY334370 for Acute Migraine: A Randomised Controlled Trial." *Lancet*. 358.9289(2001):1230-1234.

Graham et al. "Mechanism of Migraine Headache and Action of Ergotamine Tartrate." *Arch. Neurol. Psychaitry*. 39.4(1938):737-763.

Gros et al. "Aggregative Activation in Heterocyclic Chemistry. Part 5. Lithiation of Pyridine and Quinoline with the Complex Base BuLi—Me2N(CH2)2OLi (BuLi—LiDMAE)." *J. Chem. Soc., Perkin Trans. 1*. 24(1997):3597-3600.

Hall et al. "A Group Sequential Adaptive Treatment Assignment Design for Proof of Concept and Dose Selection in Headache Trials." *Contemp. Clin. Trials*. 26.3(2005):349-364.

Headache Classification Subcommittee of the International Headache Society. "The International Classification of Headache Disorders: Second Edition." *Cephalalgia*. 24.S11(2004):1-160.

Herrick-Davis et al. "Detection and Characterization of the Serotonin 5-HT 1D Receptor in Rat and Human Brain." *J. Neurochem*. 50.5(1988):1624-1631.

Ho et al. "Efficacy and Tolerability of MK-0974 (telcagepant), a New Oral Antagonist of Calcitonin Gene-Related Peptide Receptor, Compared with Zolmitriptan for Acute Migraine: A Randomised, Placebo-Controlled, Parallel-Treatment Trial." *Lancet*. 372. 9656(2008):2115-2123.

Humphrey et al. "Serotonin and Migraine." *Ann. N.Y. Acad. Sci*. 600(1990):587-598.

International Headache Society Clinical Trials Subcommittee. "Guidelines for Controlled Trials of Drugs in Migraine: Second Edition." *Cephalalgia*. 20.9(2000):765-786.

King. "Bioisosteres, Conformational Restriction, and Pro-drugs—Case History: an Example of a Conformational Restriction Approach." *Medicinal Chemistry: Principles and Practice*. King, ed. Cambridge, England: Royal Society of Chemistry. Ch. 14 (1994):206-209.

MaassenVanDenBrink et al. "Coronary Side-Effect Potential of Current and Prospective Antimigraine Drugs." *Circulation*. 98.1(1998):25-30.

Moskowitz. "Interpreting Vessel Diameter Changes in Vascular Headaches." *Cephalalgia*. 12.1(1992):5-7.

Moskowitz. "Neurogenic Inflammation in the Pathophysiology and Treatment of Migraine." *Neurol*. 43.S3(1993):S16-S20.

Nelson et al. COL-144: Preclinical Profile of a Selective 5-HT1F Receptor Agonist for Migraine. *Cephalalgia*. 29(2009):122-123: (Abstract # PC.12).

Olesen et al. "Calcitonin Gene-Related Peptide Receptor Antagonist BIBN 4096 BS for the Acute Treatment of Migraine." *N. Engl. J. Med*. 350.11(2004):1104-1110.

Phebus et al. "Characterization of LY344864 as a Pharmacological Tool to Study 5-HT1F Receptors: Binding Affinities, Brain Penetration and Activity in the Neurogenic Dural Inflammational Model of Migraine." CA 128:18603, *Life Sciences*. 61.21(1997:2117-2126.

Pringsheim et al. "Prophylaxis of Migraine Headache." *CMAJ*. 182. 7(2010):E269-276.

Radl et al. "Synthesis and Antinociceptive Activity of Some 3-Chlorophenyl- and 6-Chloro-2-Pyridinyl Derivatives." CA 130:352171. *Collection of Czechoslovak Chemical Communications*.64.2(1999):377-388.

Schoonman et al. "Migraine Headache is not Associated with Cerebral of Meningeal Vasodilation—a 3 T Magnetic Resonance Angiography Study." *Brain*. 131.Pt8(2008):2192-2200.

Stovner et al. "The Global Burden of Headache: A Documentation of Headache Prevalence and Disablity Worldwide." *Cephalalgia*. 27.3(2007):193-210.

Streitwieser et al. "Metallation." *Introduction to Organic Chemistry*. eds. Upper Saddie River, NJ: Prentice Hall. (1992):1011-1012.

Visser et al. "Chest Symptoms After Sumatriptan: A Two-Year Clinical Practice Review in 735 Consecutive Migraine Patients." *Cephalalgia*. 16.8(1996):554-559.

Weinshank et al. "Human Serotonin 1D Receptor is Encoded by a Subfamily of Two Distinct Genes: 5-HT1Dα and 5-HT1Dβ." *PNAS*. 89.8(1992):3630-3634.

Welch et al. "Tolerability of Sumatriptan: Clinical Trials and Post-Marketing Experience." *Cephalalgia*. 20.8(2000):687-695.

US 8,697,876 B2

COMPOSITIONS AND METHODS OF SYNTHESIS OF PYRIDINOLYPIPERIDINE 5-HT1F AGONISTS

RELATED APPLICATIONS

This application is a national stage application filed under 35 U.S.C. §371 of International Application No. PCT/US2011/030740, filed Mar. 31, 2011, which claims priority to, and the benefit of, U.S. Provisional Application Ser. No. 61/320,517, filed Apr. 2, 2010. The entire content of which is incorporated by reference herein.

FIELD OF THE INVENTION

The present invention is directed to a certain polymorph of the hemisuccinate salt of 2,4,6-trifluoro-N-[6-(1-methyl-piperidine-4-carbonyl)-pyridin-2-yl]-benzamide useful for activating 5-HT$_{1F}$ receptors and for the treatment or prevention of migraine. The present invention also relates to a process for the synthesis of pyridinoylpiperidine compounds of Formula I in high yield and high purity and in particular, a process to prepare 2,4,6-trifluoro-N-[6-(1-methyl-piperidine-4-carbonyl)-pyridin-2-yl]-benzamide, its hemisuccinate salt and polymorph (Form A).

BACKGROUND OF THE INVENTION

Until recently, theories regarding the pathophysiology of migraine have been dominated since 1938 by the work of Graham and Wolff. *Arch. Neurol. Psychiatry*, 39:737-63, 1938. They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, induce contraction of cephalic vascular smooth muscle and are effective in the treatment of migraine. Humphrey, et al., *Ann. NY Acad. Sci.*, 600:587-600, 1990. Recent work by Moskowitz has shown, however, that the occurrence of migraine headaches is independent of changes in vessel diameter. *Cephalalgia*, 12:5-7, 1992.

Moskowitz has proposed that currently unknown triggers for pain stimulate trigeminal ganglia that innervate vasculature within the cephalic tissue, giving rise to release of vasoactive neuropeptides from axons on the vasculature. These released neuropeptides then activate a series of events, a consequence of which is pain. This neurogenic inflammation is activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology*, 43(suppl. 3):S16-S20 1993. Sumatriptan, in fact, has high affinity for the 5-HT$_{1B}$ and 5-HT$_{1D}$ receptors, K$_i$=10.3 nM and 5.1 nM, respectively, which activity may be indicative of vasoconstrictive activity. Sumatriptan and similar compounds previously advanced for the treatment of migraine had tended to be selected on the basis of this vasoconstrictive activity under the premises of the prior art models for migraine.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. Proc. Natl. Acad. Sci. USA, 90:408-412, 1993. This 5-HT$_{1F}$ receptor exhibits a pharmacological profile distinct from any serotonergic receptor yet described. It was found that sumatriptan, in addition to the above mentioned strong affinities for the 5-HT$_{1B}$ and 5-HT$_{1D}$ receptors, also has affinity for this receptor subtype, with a K$_i$ of about 23 nM. This suggests a possible role of the 5-HT$_{1F}$ receptor in migraine.

Various 5-HT$_{1F}$ receptor agonists have subsequently been developed which have shown relative selectivity for the 5-HT$_{1F}$ receptor subclass and it has been shown that such selectivity generally reduces the vasoconstrictive activity characteristic of other compounds advanced as potential agents for the treatment of migraine and associated disorders.

Included among these 5-HT$_{1F}$ receptor agonists are compounds disclosed in the following:

U.S. Pat. Nos. 5,708,187 and 5,814,653, describing a family of 6-substituted-3-amino(alkyl)-tetrahydrocarbazoles and 7-substituted-4-amino(alkyl)cyclohepta[7,6b]Indoles;

U.S. Pat. Nos. 5,521,196, 5,721,252, 5,521,197, and WO 96/29075, describing various families of 5-substituted piperidin-3-yl-indoles and 5-substituted 1,2,3,6 tetrahydropyridin-3-yl-indoles;

WO 97/13512 describing a family of 5-substituted 3-aminoethylindoles;

WO 98/46570 describing a family of 5-substituted indoles, pyrrolo[3,2-b]pyridines, benzofurans, and benzothiophenes, having the 3-position substituted with octahydroindolizinyl, octahydro-2H-quinolizinyl, decahydropyrido[1,2-a]azepinyl, 1,2,3,5,8,8a-hexahydroindolizinyl, 1,3,4,6,9,9a-hexahydro-2H-quinolizinyl, or 1,4,6,7,8,9,10,10a-octahydropyrido[1,2-a]azepinyl;

WO 98/20875 and WO 99/25348 describing two families of 5-substituted piperidin-3-yl-azaindoles and 5-substituted 1,2,3,6-tetrahydropyridin-3-yl-azaindoles;

WO 00/00487 describing a family of 5-substituted (piperidin-3-yl or 1,2,3,6-tetrahydropyridin-3-yl)indoles, azaindoles, benzofurans, and benzothiophenes;

WO 98/08502 describing a family of 8-substituted-1,2,3,4-tetrahydro-2-dibenzofuranamines and 9-substituted-2-aminocyclohepta[b]benzofurans;

WO 98/55115 describing a family of 3-amino-1,2,3,4-tetrahydro-9H-carbazole-6-carboxamides and 4-amino-10H-cyclohepta[7,6-b]indole-7-carboxamides;

WO 98/15545 describing a select family of 3,5-disubstituted indoles and benzofurans;

WO 00/00490 describing a family of 5-allyl-substituted (piperidin-3-yl or 1,2,3,6-tetrahydropyridin-3-yl)indoles, azaindoles, benzofurans, and benzothiophenes;

WO 00/47559 describing a family of 4-(3-substituted-benzoyl)piperidines;

WO 00/50426 describing a family of 3,5-disubstituted azabenzofurans; and

WO 00/34266 describing a family of 3-heteroaryl-5-[2-(aryl or heteroaryl)-2-oxoethyl]indoles.

There is an ongoing need for an improved method and process of synthesis for the pyridinoylpiperidine compounds described herein, where the yield is improved and the purity of the resulting compounds is improved, and larger scale synthesis is possible in support of development and ultimately commercialization. This application describes such improved methods of synthesis.

SUMMARY OF THE INVENTION

The present invention relates to a certain polymorph of the hemisuccinate salt of 2,4,6-trifluoro-N-[6-(1-methyl-piperidine-4-carbonyl)-pyridin-2-yl]-benzamide useful for activating 5-HT$_{1F}$ receptors and for the treatment or prevention of migraine. The present invention also relates to the field of synthesizing pyridinoylpiperidine compounds.

The present invention relates to a polymorph of the hemisuccinate salt of 2,4,6-trifluoro-N-[6-(1-methyl-piperidine-4-carbonyl)-pyridin-2-yl]-benzamide (Form A) characterized by an X-ray diffraction pattern substantially similar to that set forth in FIG. 1A.

In some embodiments, the present invention relates to a polymorph of the hemisuccinate salt of 2,4,6-trifluoro-N-[6-(1-methyl-piperidine-4-carbonyl)-pyridin-2-yl]-benzamide (Form A) where the X-ray diffraction pattern using Cu—K$_\alpha$ radiation includes peaks at about 15.3, 16.4, 19.3, 22.1, 23.6 and 25.9 degrees 2θ. In some embodiments, the X-ray diffraction includes one or more additional peaks set forth in Table 1.

In some embodiments, the present invention relates to a polymorph of the hemisuccinate salt of 2,4,6-trifluoro-N-[6-(1-methyl-piperidine-4-carbonyl)-pyridin-2-yl]-benzamide (Form A) characterized by having unit cell parameters at 150 Kelvin of about a=11.8 Å, b=14.8 Å, c=12.2 Å, α=90°, β=104.4, and γ angle=90°.

In some embodiments, the present invention relates to a polymorph of the hemisuccinate salt of 2,4,6-trifluoro-N-[6-(1-methyl-piperidine-4-carbonyl)-pyridin-2-yl]-benzamide (Form A) characterized by a Differential Scanning Calorimetry (DSC) thermogram having a maximum endotherm value at about 199° C.

In some embodiments, the present invention relates to a polymorph of the hemisuccinate salt of 2,4,6-trifluoro-N-[6-(1-methyl-piperidine-4-carbonyl)-pyridin-2-yl]-benzamide (Form A) where the X-ray diffraction pattern using Cu—K$_\alpha$ radiation includes peaks at about 15.3, 16.4, 19.3, 22.1, 23.6 and 25.9 degrees 2θ and a DSC thermogram having a maximum endotherm value at about 199° C.

In some embodiments, the present invention relates to a polymorph of the hemisuccinate salt of 2,4,6-trifluoro-N-[6-(1-methyl-piperidine-4-carbonyl)-pyridin-2-yl]-benzamide (Form A) characterized by an X-ray diffraction pattern substantially similar to that set forth in FIG. 1A and a DSC thermogram having a maximum endotherm value at about 199° C.

In some embodiments, the present invention relates to a polymorph of the hemisuccinate salt of 2,4,6-trifluoro-N-[6-(1-methyl-piperidine-4-carbonyl)-pyridin-2-yl]-benzamide (Form A), where the polymorph is produced by recrystallization with ethanol.

The present invention relates to a pharmaceutical composition comprising a polymorph of the hemisuccinate salt of 2,4,6-trifluoro-N-[6-(1-methyl-piperidine-4-carbonyl)-pyridin-2-yl]-benzamide (Form A) and a pharmaceutically acceptable carrier.

In some embodiments, the pharmaceutical composition comprises a polymorph of the hemisuccinate salt of 2,4,6-trifluoro-N-[6-(1-methyl-piperidine-4-carbonyl)-pyridin-2-yl]-benzamide (Form A) that is substantially free from impurities. In some embodiments, the pharmaceutical composition comprises a polymorph of the hemisuccinate salt of 2,4,6-trifluoro-N-[6-(1-methyl-piperidine-4-carbonyl)-pyridin-2-yl]-benzamide (Form A) that has a chemical purity greater than 98.0% as determined by HPLC. In some embodiments, the pharmaceutical comprises a polymorph of the hemisuccinate salt of 2,4,6-trifluoro-N-[6-(1-methyl-piperidine-4-carbonyl)-pyridin-2-yl]-benzamide (Form A) that is substantially free from the impurity:

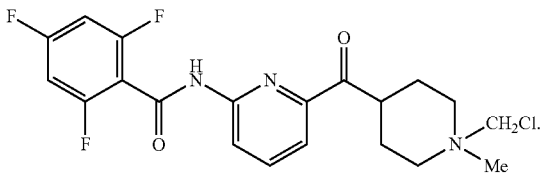

The present invention relates to a method of treating migraine in a mammal comprising administering to a mammal in need of such treatment an effective amount of a polymorph of the hemisuccinate salt of 2,4,6-trifluoro-N-[6-(1-methyl-piperidine-4-carbonyl)-pyridin-2-yl]-benzamide (Form A). In some embodiments, the mammal is a human.

The present invention relates to a process for preparing 2,4,6-trifluoro-N-[6-(1-methyl-piperidine-4-carbonyl)-pyridin-2-yl]-benzamide or a salt thereof. In some embodiments, the salt is a pharmaceutically acceptable salt thereof. In some embodiments, the salt is the hemisuccinate salt.

The present invention relates to a process for preparing 2,4,6-trifluoro-N-[6-(1-methyl-piperidine-4-carbonyl)-pyridin-2-yl]-benzamide or a salt thereof comprising the step of: reacting (6-aminopyridin-2-yl)(1-methylpiperidin-4-yl)methanone or a salt thereof with 2,4,6-trifluorobenzoylchloride in the presence of chlorobenzene to yield 2,4,6-trifluoro-N-[6-(1-methyl-piperidin-4-ylcarbonyl)-piperidin-2-yl]benzamide hydrochloride.

The present invention relates to a process for preparing 2,4,6-trifluoro-N-[6-(1-methyl-piperidine-4-carbonyl)-pyridin-2-yl]-benzamide or a salt thereof, comprising the step of: reacting (6-bromopyridin-2-yl)(1-methylpiperidin-4-yl)methanone hydrobromide with >0.02 wt % copper(I)oxide at less than 80° C. to yield (6-aminopyridin-2-yl)(1-methylpiperidin-4-yl)methanone.

The present invention relates to a process for preparing 2,4,6-trifluoro-N-[6-(1-methyl-piperidine-4-carbonyl)-pyridin-2-yl]-benzamide or a salt thereof, further comprising the step of: reacting N,N-diethyl-1-methylpiperidine-4-carboxamide with a solution of 2,6-dibromopyridine and Grignard reagent followed by the addition hydrobromic acid to yield (6-bromopyridin-2-yl)(1-methylpiperidin-4-yl)methanone hydrobromide.

The present invention relates to a process for preparing 2,4,6-trifluoro-N-[6-(1-methyl-piperidine-4-carbonyl)-pyridin-2-yl]-benzamide or salt thereof, further comprising the step of: reacting 1-methylpiperidine-4-carboxylic acid with thionyl chloride and diethyl amine to yield N,N-diethyl-1-methylpiperidine-4-carboxamide.

The present invention relates to a process for preparing 2,4,6-trifluoro-N-[6-(1-methyl-piperidine-4-carbonyl)-pyridin-2-yl]-benzamide or a salt thereof, further comprising the step of: converting piperidine-4-carboxylic acid to 1-methylpiperidine-4-carboxylic acid using transfer hydrogenation conditions.

The present invention relates to a process for preparing 2,4,6-trifluoro-N-[6-(1-methyl-piperidine-4-carbonyl)-pyridin-2-yl]-benzamide hemisuccinate salt further comprising the step of: converting 2,4,6-trifluoro-N-[6-(1-methyl-piperidin-4-ylcarbonyl)-piperidin-2-yl]benzamide hydrochloride using succinic acid in the presence of ethanol to yield 2,4,6-trifluoro-N-[6-(1-methyl-piperidin-4-ylcarbonyl)-piperidin-2-yl]benzamide hemi-succinate salt.

The present invention relates to a process for preparing a compound of formula I:

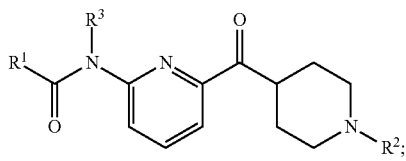

or pharmaceutically acceptable acid addition salts thereof, where;

$R^1$ is phenyl substituted with one to three halo substituents;
$R^2$ is $C_1$-$C_3$ alkyl; and
$R^3$ is hydrogen or $C_1$-$C_3$ alkyl, comprising the steps of:

(1) converting piperidine-4-carboxylic acid to a compound of formula IA:

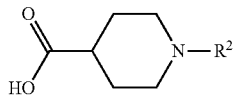

using acid using transfer hydrogenation conditions;

(2) reacting a compound of formula IA with thionyl chloride and diethyl amine to yield a compound of formula IB:

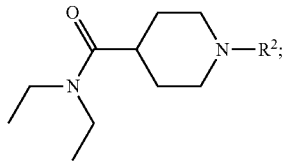

(3) reacting a compound of formula IC with a solution of 2,6-dibromopyridine and Grignard reagent followed by treatment with hydrobromic acid to the salt of formula IC:

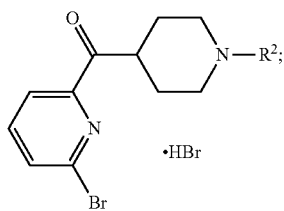

(4) reacting a salt of formula IC with >0.02 wt % copper (I)oxide at less than 80° C. to yield a compound of formula ID:

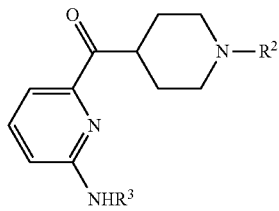

and (5) reacting a compound of formula ID with 2,4,6-trifluorobenzoylchloride in the presence of chlorobenzene to yield a compound of formula I.

BRIEF DESCRIPTION OF THE FIGURES

FIG. 1 shows X-ray diffraction patterns for various forms of the Compound VIII.

DETAILED DESCRIPTION OF THE INVENTION

Figure 1A:
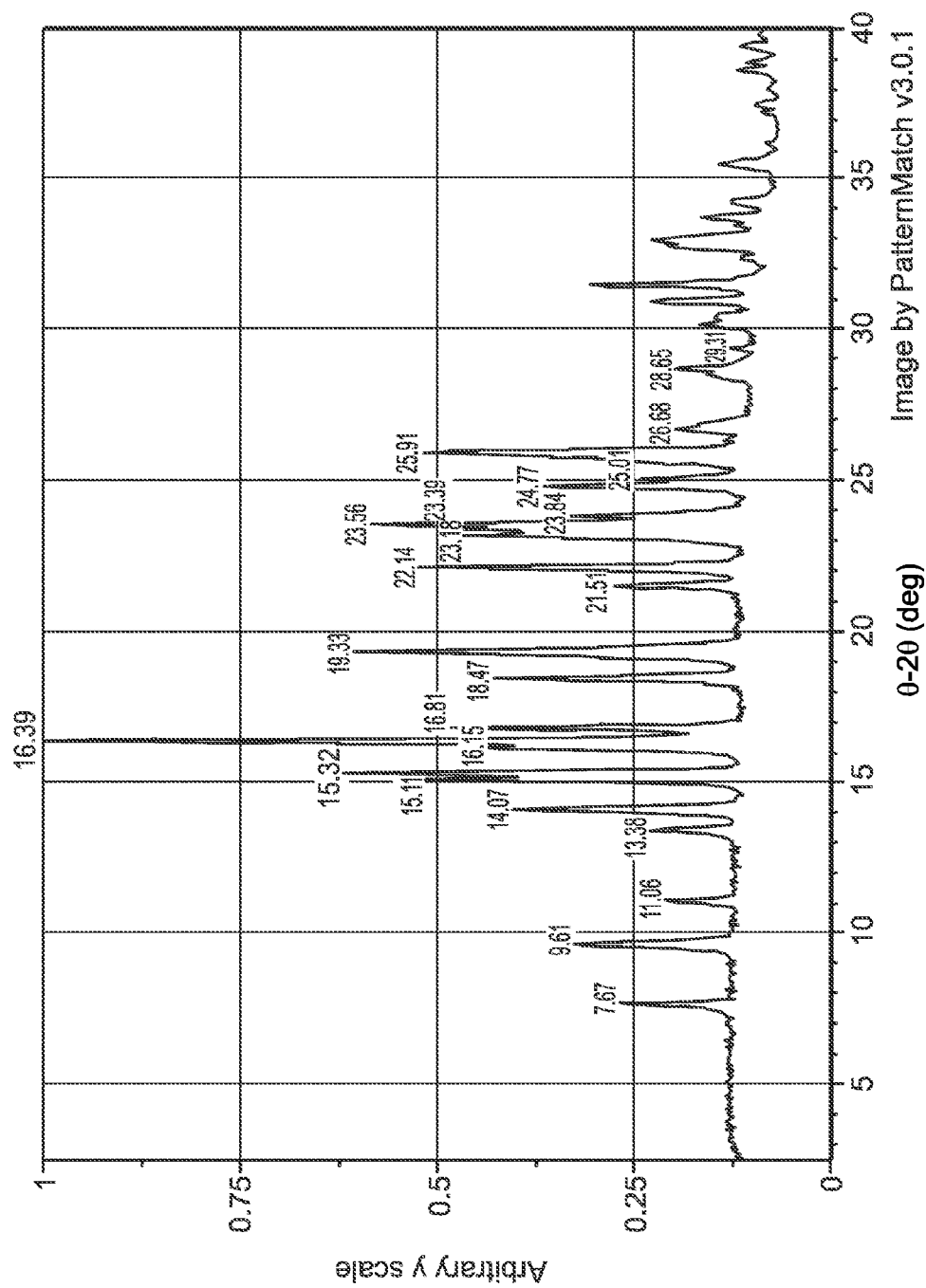
FIG. 1A: Form A.

U.S. Pat. No. 7,423,050 and U.S. Publication No. 20080300407 describe pyridinoylpiperidine compounds that are useful for activating the serotonin-1F (5-$HT_{1F}$) receptor and for the treatment or prevention of migraine in a mammal, including the hemisuccinate salt of 2,4,6-trifluoro-N-[6-(1-methyl-piperidine-4-carbonyl)-pyridin-2-yl]-benzamide (Compound VIII) having the structural formula:

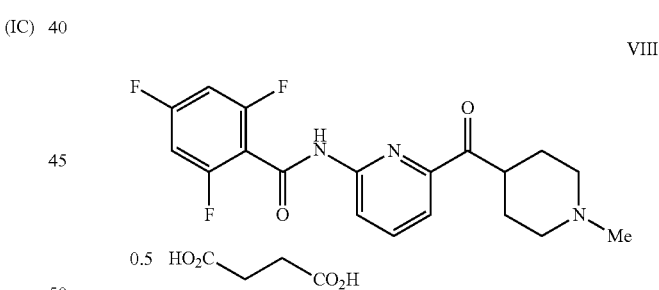

The aforementioned patent and publication do not refer to any specific polymorph forms of the hemisuccinate salt of 2,4,6-trifluoro-N-[6-(1-methyl-piperidine-4-carbonyl)-pyridin-2-yl]-benzamide. Crystallinity of drugs affects, among other physical and mechanical properties, their solubility, dissolution rate, hardness, compressability and melting point. Because these properties may, in turn, affect a drug's manufacture and its utility, there is an existing need in the chemical and therapeutic arts for identification of crystalline forms of drugs and ways of making them. It has now been discovered that the hemisuccinate salt of 2,4,6-trifluoro-N-[6-(1-methyl-piperidine-4-carbonyl)-pyridin-2-yl]-benzamide can exist as a novel crystalline form, in particular Form A. Form A is an anhydrous crystal form.

The present invention is directed to a certain polymorph of the hemisuccinate salt of 2,4,6-trifluoro-N-[6-(1-methyl-piperidine-4-carbonyl)-pyridin-2-yl]-benzamide characterized by its X-ray diffraction pattern and/or DSC thermogram, methods of making this polymorph, pharmaceutical compositions comprising this polymorph and methods of treating or preventing migraine by administering this polymorph to a subject.

The present invention is directed to a certain polymorph of the hemisuccinate salt of 2,4,6-trifluoro-N-[6-(1-methyl-piperidine-4-carbonyl)-pyridin-2-yl]-benzamide (Form A) characterized by the principal X-ray diffraction pattern peaks expressed in terms of 2θ and d-spacings, for example, as measured using Cu—K$_\alpha$ radiation.

The present invention is directed to a certain polymorph of the hemisuccinate salt of 2,4,6-trifluoro-N-[6-(1-methyl-piperidine-4-carbonyl)-pyridin-2-yl]-benzamide (Form A) characterized by an X-ray diffraction pattern, using Cu—K$_\alpha$ radiation, including peaks at about 15.3, 16.4, 19.3, 22.1, 23.6 and 25.9 degrees 2θ. In some embodiments, this certain polymorph of the hemisuccinate salt of 2,4,6-trifluoro-N-[6-(1-methyl-piperidine-4-carbonyl)-pyridin-2-yl]-benzamide (Form A) is also characterized by an X-ray diffraction pattern, using Cu—K$_\alpha$ radiation, including one or more further peaks identified in Table 1. In some embodiments, this certain polymorph of the hemisuccinate salt of 2,4,6-trifluoro-N-[6-(1-methyl-piperidine-4-carbonyl)-pyridin-2-yl]-benzamide (Form A) is also characterized by an X-ray diffraction pattern substantially similar to that set forth in FIG. 1A. In some embodiments, this certain polymorph of the hemisuccinate salt of 2,4,6-trifluoro-N-[6-(1-methyl-piperidine-4-carbonyl)-pyridin-2-yl]-benzamide (Form A) is also characterized by having unit cell parameters at 150 Kelvin of about a=11.8 Å, b=14.8 Å, c=12.2 Å, α=90°, β=104.4, and γ angle=90°.

The present invention is also directed to a polymorph of the hemisuccinate salt of 2,4,6-trifluoro-N-[6-(1-methyl-piperidine-4-carbonyl)-pyridin-2-yl]-benzamide (Form A) characterized by a Differential Scanning Calorimetry (DSC) thermogram having a maximum value at about 199° C., as measured, for example, using a TA Instruments differential scanning calorimeter 2920 or Q2000.

A further embodiment of the present invention is a polymorph of the hemisuccinate salt of 2,4,6-trifluoro-N-[6-(1-methyl-piperidine-4-carbonyl)-pyridin-2-yl]-benzamide (Form A) characterized by an X-ray diffraction pattern substantially similar to that set forth in FIG. 1A and a Differential Scanning Calorimetry (DSC) thermogram having a single maximum value at about 199° C.

The present invention is directed to a polymorph of the hemisuccinate salt of 2,4,6-trifluoro-N-[6-(1-methyl-piperidine-4-carbonyl)-pyridin-2-yl]-benzamide (Form A) produced by recrystallization with ethanol.

The present invention is directed to a pharmaceutical composition comprising the a polymorph of the hemisuccinate salt of 2,4,6-trifluoro-N-[6-(1-methyl-piperidine-4-carbonyl)-pyridin-2-yl]-benzamide (Form A) and a pharmaceutically acceptable carrier.

The present invention is directed to a method of treating migraine in a mammal comprising administering to a mammal in need of such treatment an effective amount of a polymorph of the hemisuccinate salt of 2,4,6-trifluoro-N-[6-(1-methyl-piperidine-4-carbonyl)-pyridin-2-yl]-benzamide (Form A). In one embodiment, the mammal is a human.

The present invention is directed to a method of preventing migraine in a mammal comprising administering to a mammal in need of such treatment an effective amount of a polymorph of the hemisuccinate salt of 2,4,6-trifluoro-N-[6-(1-methyl-piperidine-4-carbonyl)-pyridin-2-yl]-benzamide (Form A). In one embodiment, the mammal is a human.

One embodiment of the present invention is a method for increasing activation of 5-HT$_{1F}$ receptors by administering a polymorph of the hemisuccinate salt of 2,4,6-trifluoro-N-[6-(1-methyl-piperidine-4-carbonyl)-pyridin-2-yl]-benzamide (Form A), while avoiding vasoconstrictive activity, for treating a variety of disorders that have been linked to decreased neurotransmission of serotonin in mammals. Included among these disorders are migraine, general pain, trigeminal neuralgia, dental pain or temperomandibular joint dysfunction pain, anxiety, general anxiety disorder, panic disorder, depression, disorders of sleep, chronic fatigue syndrome, premenstrual syndrome or late luteal phase syndrome, post-traumatic syndrome, memory loss, dementia including dementia of aging, social phobia, autism, attention deficit hyperactivity disorder, disruptive behavior disorders, impulse control disorders, borderline personality disorder, obsessive compulsive disorder, premature ejaculation, erectile dysfunction, bulimia, anorexia nervosa, alcoholism, tobacco abuse, mutism, and trichotillomania. The polymorph of this invention is also useful as a prophylactic treatment for migraine. Any of the described methods may employ a polymorph of the hemisuccinate salt of 2,4,6-trifluoro-N-[6-(1-methyl-piperidine-4-carbonyl)-pyridin-2-yl]-benzamide (Form A).

In those instances where the disorders which can be treated by serotonin agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The use of a polymorph of the hemisuccinate salt of 2,4,6-trifluoro-N-[6-(1-methyl-piperidine-4-carbonyl)-pyridin-2-yl]-benzamide (Form A) for the activation of the 5-HT$_{1F}$ receptor, for the inhibition of neuronal peptide extravasation, in general or due to stimulation of the trigeminal ganglia specifically, and/or for the treatment of any of the disorders described above, are all embodiments of the present invention.

The present invention is further directed to processes for the preparation of a compound having the formula I:

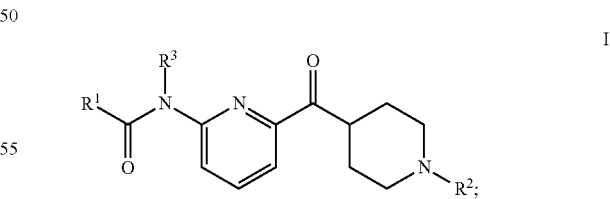

or salts thereof, where R$^1$ is phenyl substituted with one to three halo substituents; R$^2$ is C$_1$-C$_3$ alkyl; and R$^3$ is hydrogen or C$_1$-C$_3$ alkyl. The present invention includes processes for the preparation of a polymorph of a compound of formula I. The present invention includes processes for the preparation of a pharmaceutically acceptable acid addition salt thereof.

The present invention is directed to a process for the preparation of a compound of formula I or salt thereof comprising the steps of:

(1) converting piperidine-4-carboxylic acid to a compound of formula IA:

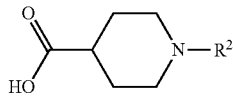

(IA)

using acid using transfer hydrogenation conditions;

(2) reacting a compound of formula IA with thionyl chloride and diethyl amine to yield a compound of formula IB:

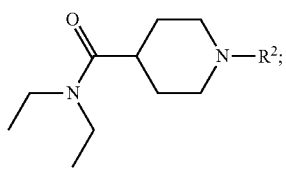

(IB)

(3) reacting a compound of formula IB with a solution of 2,6-dibromopyridine and Grignard reagent followed by treatment with hydrobromic acid to the salt of formula IC:

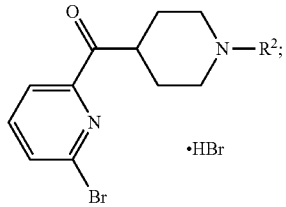

(IC)

(4) reacting a salt of formula IC with >0.02 wt % copper (I)oxide at less than 80° C. to yield a compound of formula ID:

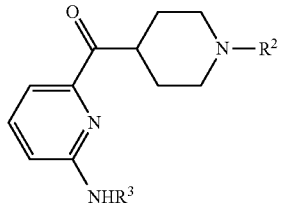

(ID)

and (5) reacting a compound of formula ID with 2,4,6-trifluorobenzoylchloride in the presence of chlorobenzene to yield a compound of formula I.

The present invention is directed to a process for preparing the polymorph of the hemisuccinate salt of 2,4,6-trifluoro-N-[6-(1-methyl-piperidine-4-carbonyl)-pyridin-2-yl]-benzamide (Form A).

The present invention is directed to a process for preparing the polymorph the hemisuccinate salt of 2,4,6-trifluoro-N-[6-(1-methyl-piperidine-4-carbonyl)-pyridin-2-yl]-benzamide (Form A) comprising the step of: converting 2,4,6-trifluoro-N-[6-(1-methyl-piperidin-4-ylcarbonyl)-piperidin-2-yl]benzamide or a salt thereof using succinic acid in the presence of ethanol to yield 2,4,6-trifluoro-N-[6-(1-methyl-piperidin-4-ylcarbonyl)-piperidin-2-yl]benzamide hemi-succinate salt. In some embodiments, the starting salt is 2,4,6-trifluoro-N-[6-(1-methyl-piperidin-4-ylcarbonyl)-piperidin-2-yl]benzamide hydrochloride.

The present invention is directed to a pharmaceutical composition comprising a polymorph of the hemisuccinate salt of 2,4,6-trifluoro-N-[6-(1-methyl-piperidine-4-carbonyl)-pyridin-2-yl]-benzamide (Form A), wherein said polymorph is substantially free from impurities. The term "chemical purity" as used herein, means percentage of a particular compound in a sample. Unless stated otherwise, percentages stated throughout this specification are weight/weight (w/w) percentages. In one aspect, said polymorph has a chemical purity greater than 98.0% as determined by HPLC. In one aspect, said polymorph has a chemical purity of 99.0%. In one aspect, said polymorph has a chemical purity of 99.5%. In one aspect, said polymorph has a chemical purity of 99.6%. In one aspect, said polymorph has a chemical purity of 99.7%. In one aspect, said is polymorph is substantially free from the impurity

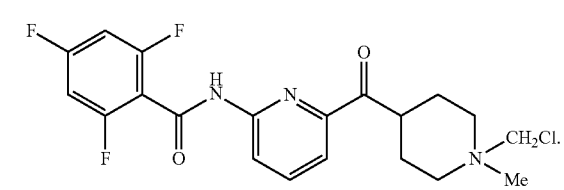

In one embodiment, the impurity is

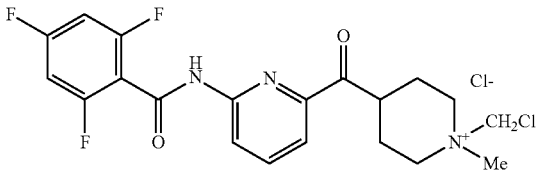

1-(chloromethyl)-1-methyl-4-(6-(2,4,6-trifluorobenzamido)picolinoyl)piperidin-1-ium The term "crystalline" as used herein, means having a regularly repeating arrangement of molecules or external face planes. The term "crystalline purity" as used herein, means percentage of a crystalline compound in a sample which may contain an amorphous form of the same compound, at least one other crystalline form of the compound or a mixture thereof. In one aspect, said polymorph has a crystalline purity of about 97.0%.

In one aspect, said polymorph has a crystalline purity of about 99.0% crystalline purity. In one aspect, said polymorph has a crystalline purity of about 100% crystalline purity. In one aspect, differential scanning calorimetry (DSC) is used for determination of whether more than one phase is present.

The present invention is directed to a pharmaceutical composition comprising a polymorph of the hemisuccinate salt of 2,4,6-trifluoro-N-[6-(1-methyl-piperidine-4-carbonyl)-pyridin-2-yl]-benzamide (Form A), where the composition is a commercial scale composition.

Scheme 1 illustrates a process for preparing the hemisuccinate salt of 2,4,6-trifluoro-N-[6-(1-methyl-piperidine-4-carbonyl)-pyridin-2-yl]-benzamide.

salt thereof. In some embodiment, the salt thereof is a pharmaceutically acceptable salt. In some embodiments, the salt thereof is 2,4,6-trifluoro-N-[6-(1-methyl-piperidine-4-car-

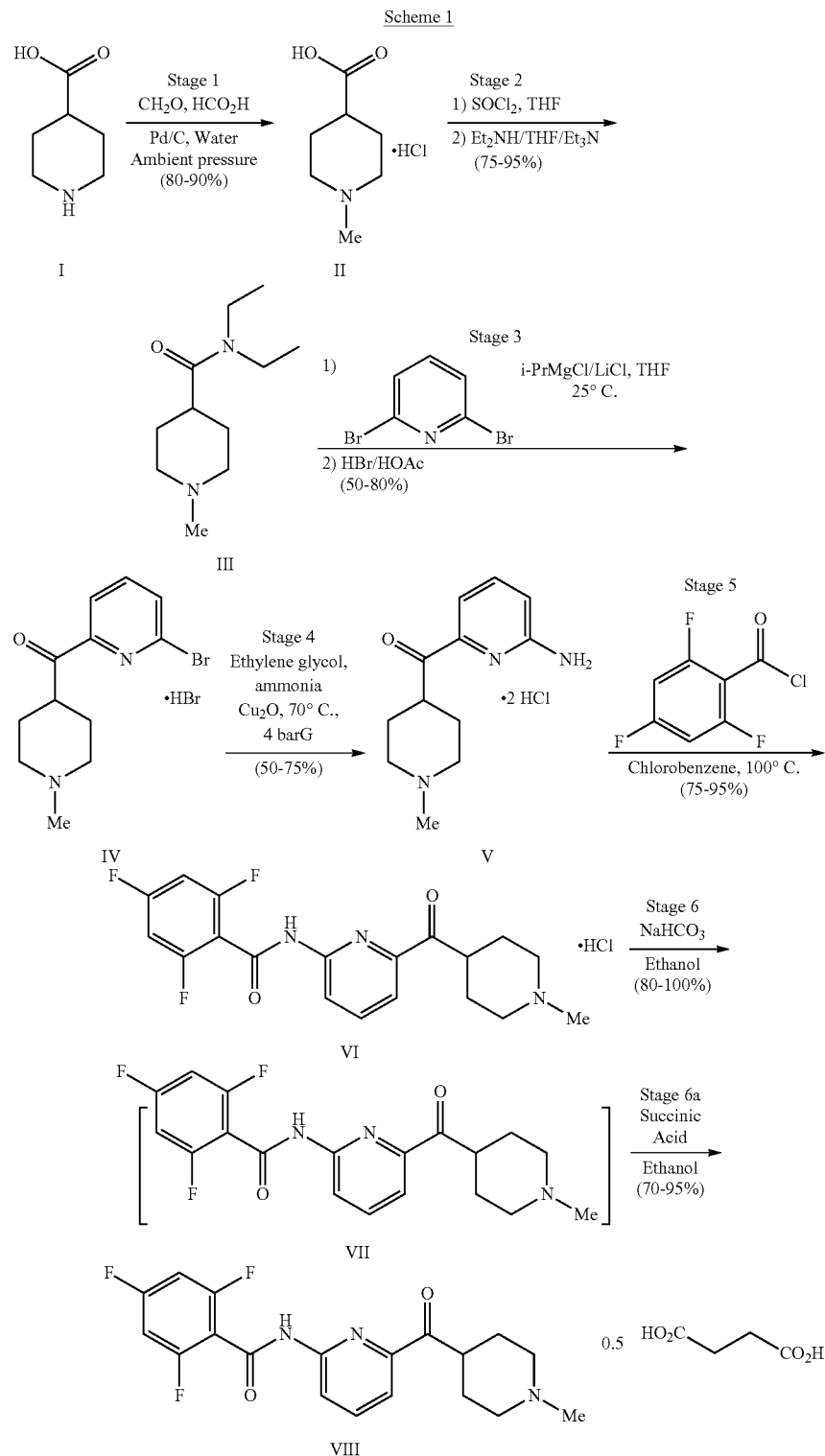

The present invention is directed to a process as described below for preparing 2,4,6-trifluoro-N-[6-(1-methyl-piperidine-4-carbonyl)-pyridin-2-yl]-benzamide or a bonyl)-pyridin-2-yl]-benzamide hemisuccinate salt. The present invention is directed to the process comprising the steps of:

(1) converting piperidine-4-carboxylic acid to 1-methylpiperidine-4-carboxylic acid or a salt thereof using transfer hydrogenation conditions;

(2) reacting 1-methylpiperidine-4-carboxylic acid with thionyl chloride and diethyl amine to yield N,N-diethyl-1-methylpiperidine-4-carboxamide;

(3) reacting N,N-diethyl-1-methylpiperidine-4-carboxamide with a solution of 2,6-dibromopyridine and Grignard reagent followed by hydrobromic acid to yield (6-bromopyridin-2-yl)(1-methylpiperidin-4-yl)methanone hydrobromide;

(4) reacting (6-bromopyridin-2-yl)(1-methylpiperidin-4-yl)methanone hydrobromide with >0.02 wt % copper(I)oxide at less than 80° C. to yield (6-aminopyridin-2-yl)(1-methylpiperidin-4-yl)methanone or a salt thereof; and (5) reacting (6-aminopyridin-2-yl)(1-methylpiperidin-4-yl)methanone with 2,4,6-trifluorobenzoylchloride in the presence of chlorobenzene to yield 2,4,6-trifluoro-N-[6-(1-methyl-piperidin-4-ylcarbonyl)-piperidin-2-yl]benzamide or a pharmaceutically acceptable salt thereof. In some embodiments, the pharmaceutically acceptable salt produced in step 5 is the hydrochloride salt.

The present invention is directed to a process for the preparation of the hemi-succinate salt of 2,4,6-trifluoro-N-[6-(1-methyl-piperidine-4-carbonyl)-pyridin-2-yl]-benzamide further comprising the step of converting 2,4,6-trifluoro-N-[6-(1-methyl-piperidin-4-ylcarbonyl)-piperidin-2-yl]
benzamide hydrochloride using succinic acid in the presence of ethanol to yield 2,4,6-trifluoro-N-[6-(1-methyl-piperidin-4-ylcarbonyl)-piperidin-2-yl]benzamide hemi-succinate salt.

The present invention is directed to a process the preparation of the hemi-succinate salt of 2,4,6-trifluoro-N-[6-(1-methyl-piperidine-4-carbonyl)-pyridin-2-yl]-benzamide, where the process is a commercial scale process.

Step 1

The present invention is directed to a process for preparing 2,4,6-trifluoro-N-[6-(1-methyl-piperidine-4-carbonyl)-pyridin-2-yl]-benzamide or a pharmaceutically acceptable salt thereof e.g., the hemi-succinate salt comprising the step of: converting piperidine-4-carboxylic acid (I) to 1-methylpiperidine-4-carboxylic acid (II) or a pharmaceutically acceptable salt thereof (e.g., to the hydrochloride salt) using transfer hydrogenation conditions. In some embodiments, the present invention is directed to a process for preparing 2,4,6-trifluoro-N-[6-(1-methyl-piperidine-4-carbonyl)-pyridin-2-yl]-benzamide hemisuccinate salt comprising the step of: reacting piperidine-4-carboxylic acid (I) with formaldehyde at ambient pressure to yield 1-methylpiperidine-4-carboxylic acid (II). It is advantageous to convert the piperidine-4-carboxylic acid (isonipecotic acid) to 1-methylpiperidine-4-carboxylic acid using transfer hydrogenation conditions. Transfer hydrogenation is the addition of hydrogen to a molecule from a source other than gaseous $H_2$.

Transfer hydrogenation offers several advantages including ease of handling in a wide variety of reaction vessels and avoids the need for specialized high pressure equipment. In one aspect, transfer hydrogenation conditions include using formaldehyde. In one aspect, transfer hydrogenation conditions include ambient pressure. In one aspect, transfer hydrogenation conditions include a palladium catalyst e.g., palladium on charcoal, or platinum. In one aspect, transfer hydrogenation conditions include water and acid e.g., formic acid. In one aspect, the transfer hydrogenation conditions include heat. In one aspect, the reaction mixture is heated from ambient to about 90 to 95° C.

In one aspect, 1-methylpiperidine-4-carboxylic acid (II) is converted to the hydrochloride salt. In one aspect, the hydrochloride salt of 1-methylpiperidine-4-carboxylic acid (II) is formed using hydrochloric acid e.g., 1.5 equivalents.

Step 2.

The present invention is directed to a process for preparing 2,4,6-trifluoro-N-[6-(1-methyl-piperidine-4-carbonyl)-pyridin-2-yl]-benzamide or a pharmaceutically acceptable salt thereof e.g., the hemisuccinate salt comprising the step of: reacting 1-methylpiperidine-4-carboxylic acid (II) with thionyl chloride and diethyl amine to yield N,N-diethyl-1-methylpiperidine-4-carboxamide (III). In some embodiments, the hydrochloride salt of II is reacted with thionyl chloride and diethyl amine.

The present invention is directed to a process for preparing the hemi-succinate salt of 2,4,6-trifluoro-N-[6-(1-methyl-piperidine-4-carbonyl)-pyridin-2-yl]-benzamide, where in step 2, the use of diethylamine for the conversion of 1-methylpiperidine-4-carboxylic acid (II) or a salt thereof to N,N-diethyl-1-methylpiperidine-4-carboxamide (III) is advantageous over the use and formation of other dialkylamines e.g., dimethylamine. For example, ethylamine is a liquid at ambient temperature and thus, diethylamine offers ease of handling over dimethylamine.

The present invention is directed to a process for preparing the hemi-succinate salt of 2,4,6-trifluoro-N-[6-(1-methyl-piperidine-4-carbonyl)-pyridin-2-yl]-benzamide, where the reagent used to activate the carboxylic acid moiety is thionyl chloride. The use of thionyl chloride for the conversion of 1-methylpiperidine-4-carboxylic acid (II) or a salt thereof to N,N-diethyl-1-methylpiperidine-4-carboxamide (III) is advantageous. Specifically, the use of thionyl chloride avoids the formation of dimethyl carbamoyl chloride:

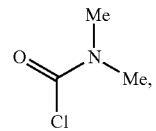

which is a carcinogen known to form as a result of the use of another alternative reagents such as oxalyl chloride and DMF. In one aspect, N,N-diethyl-1-methylpiperidine-4-carboxamide (III) is formed substantially free of dimethyl carbamoyl chloride.

Step 3.

The present invention is directed to a process for preparing 2,4,6-trifluoro-N-[6-(1-methyl-piperidine-4-carbonyl)-pyridin-2-yl]-benzamide or a pharmaceutically acceptable salt thereof e.g., the hemi-succinate salt comprising the step of: reacting N,N-diethyl-1-methylpiperidine-4-carboxamide (III) with a solution of 2,6-dibromopyridine and Grignard reagent followed by the addition of hydrobromic acid to yield (6-bromopyridin-2-yl)(1-methylpiperidin-4-yl)methanone (IV) hydrobromide.

The present invention is directed to a process for preparing the hemi-succinate salt of 2,4,6-trifluoro-N-[6-(1-methyl-piperidine-4-carbonyl)-pyridin-2-yl]-benzamide, where the use of Grignard methodology in the formation of (6-bromopyridin-2-yl)(1-methylpiperidin-4-yl)methanone (IV) is advantageous over other methodologies e.g., methods employing lithium reagents such as butyllithium. The Grignard process is carried out at ambient temperature and thus circumvents the need for specialized cryogenic equipment required for the use of lithium reagents. Ambient temperature is approximately 18-25° C. In one aspect, the Grignard reagent is isopropyl Grignard reagent. In one aspect, the Grignard reagent is Turbo Grignard reagent. Turbo Grignard reagent is lithium chloride plus Grignard reagent. In one aspect, the Turbo Grignard is isopropylmagnesium chloride/lithium chloride.

Formation of the hydrobromide salt of (6-bromopyridin-2-yl)(1-methylpiperidin-4-yl)methanone (intermediate IV, shown in Scheme 1) is advantageous. For example, formation of the hydrochloride salt of intermediate IV gives rise to an undesired by-product resulting from chloride exchange with the bromine on the pyridine ring. The undesired chlorinated by-product is:

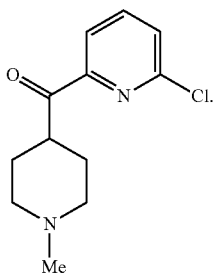

(Va)

This chlorinated by-product does not displace with ammonia in the subsequent step 4, thus lowering yield in conversion of IV to V. The use of the HBr salt of (6-bromopyridin-2-yl)(1-methylpiperidin-4-yl)methanone (IV) circumvents this side reaction and thus increases yields and purity in conversion of IV to V. In one aspect, (6-aminopyridin-2-yl)(1-methylpiperidin-4-yl)methanone is formed substantially free from the chlorinated by-product Va.

Step 4.

The present invention is directed to a process for preparing 2,4,6-trifluoro-N-[6-(1-methyl-piperidine-4-carbonyl)-pyridin-2-yl]-benzamide or a pharmaceutically acceptable salt thereof e.g., the hemi-succinate salt comprising the step of: reacting (6-bromopyridin-2-yl)(1-methylpiperidin-4-yl)methanone (IV) hydrobromide with >0.02 wt % copper(I) oxide at less than 80° C. to yield (6-aminopyridin-2-yl)(1-methylpiperidin-4-yl)methanone(V) or a pharmaceutically acceptable salt thereof e.g., the hydrochloride salt.

The present invention is directed to a process for preparing the hemi-succinate salt of 2,4,6-trifluoro-N-[6-(1-methyl-piperidine-4-carbonyl)-pyridin-2-yl]-benzamide, where the conversion of (6-bromopyridin-2-yl)(1-methylpiperidin-4-yl)methanone (IV) hydrobromide to (6-aminopyridin-2-yl)(1-methylpiperidin-4-yl)methanone (V) using ammonia and greater than 0.02 wt % copper(I)oxide is advantageous. The use of a catalyst loading of >0.02 wt % allows for the reaction to be conducted at a lower temperature, a temperature below 80° C. e.g., about 60-70° C., preferably about 70° C. The use of a lower temperature avoids discoloration of the product of step 4, (6-aminopyridin-2-yl)(1-methylpiperidin-4-yl)methanone (V), and ultimately affords the final product, 2,4,6-trifluoro-N-[6-(1-methyl-piperidine-4-carbonyl)-pyridin-2-yl]-benzamide hemisuccinate salt, as a white crystalline solid. This is in contrast to the coloration of the final product when step 4 is carried out at higher temperatures such as 80-110° C. and lower catalyst loadings≤0.02 wt %. Using these conditions, the resulting product at step 4 is yellow to brown in color and this undesired discoloration carries over to the final product which results in an off-white to brown colored final product, 2,4,6-trifluoro-N-[6-(1-methyl-piperidine-4-carbonyl)-pyridin-2-yl]-benzamide hemisuccinate salt (VIII). For preparation of a pharmaceutical composition, a white active ingredient is preferred over a colored active ingredient because a white active ingredient does not require any dye additives prior to formulation of the drug product. In step 4, it is also advantageous to replace work-up solvent dichloromethane, which can form undesired alkylation by-products such as impurity

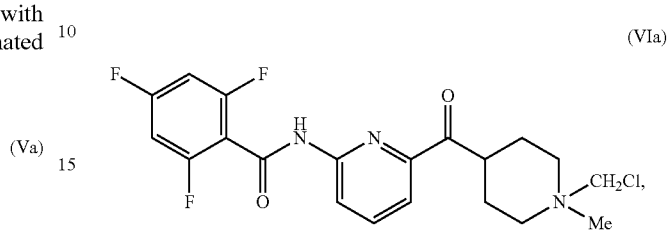

(VIa)

with unreactive ether solvent such as TBME, which is a preferred solvent.

Step 5.

The present invention is directed to a process for preparing 2,4,6-trifluoro-N-[6-(1-methyl-piperidine-4-carbonyl)-pyridin-2-yl]-benzamide or a pharmaceutically acceptable salt thereof e.g., the hemi-succinate salt comprising the step of: reacting (6-aminopyridin-2-yl)(1-methylpiperidin-4-yl)methanone (V) with 2,4,6-trifluorobenzoylchloride in the presence of chlorobenzene to yield 2,4,6-trifluoro-N-[6-(1-methyl-piperidin-4-ylcarbonyl)-piperidin-2-yl]benzamide (VI) hydrochloride.

The present invention is directed to a process for preparing the hemi-succinate salt of 2,4,6-trifluoro-N-[6-(1-methyl-piperidine-4-carbonyl)-pyridin-2-yl]-benzamide, where it is advantageous to react (6-aminopyridin-2-yl)(1-methylpiperidin-4-yl)methanone (V) with 2,4,6-trifluorobenzoylchloride in the presence of the solvent chlorobenzene. In some embodiments, the dihydrochloride salt of V is used in step 5. The use of an alternative solvent, such as dichloromethane (DCM), was found to afford a potentially genotoxic by-product:

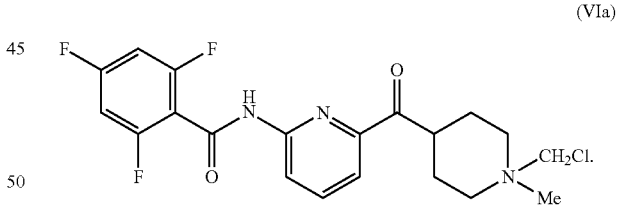

(VIa)

When chlorobenzene or other non-reactive DCM replacement such as toluene is used, formation of the by-product is not observed. In some embodiments, 2,4,6-trifluoro-N-[6-(1-methyl-piperidin-4-ylcarbonyl)-piperidin-2-yl]benzamide (VI) hydrochloride is formed substantially free of the by-product VIa.

Step 6 and 6a.

The present invention is directed to a process for preparing 2,4,6-trifluoro-N-[6-(1-methyl-piperidin-4-ylcarbonyl)-piperidin-2-yl]benzamide hemisuccinate salt comprising the step of: converting 2,4,6-trifluoro-N-[6-(1-methyl-piperidin-4-ylcarbonyl)-piperidin-2-yl]benzamide (VI) hydrochloride using succinic acid in the presence of ethanol to yield 2,4,6-trifluoro-N-[6-(1-methyl-piperidin-4-ylcarbonyl)-piperidin-2-yl]benzamide hemi-succinate salt.

The present invention is directed to a process for preparing the hemi-succinate salt of 2,4,6-trifluoro-N-[6-(1-methyl-piperidine-4-carbonyl)-pyridin-2-yl]-benzamide, where it is advantageous to convert 2,4,6-trifluoro-N-[6-(1-methyl-piperidin-4-ylcarbonyl)-piperidin-2-yl]benzamide hydrochloride to the free base and then to the hemi-succinate salt in ethanol. The use of ethanol as a crystallization solvent is preferred over solvents such as acetone and provides reproducibly a single polymorph Form A.

Definitions

The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_3$ alkyl" refers to a straight chain or branched hydrocarbon moiety having from 1 to 3 carbon atoms, including methyl, ethyl, n-propyl, and isopropyl. The term "$C_1$-$C_3$ n-alkyl" refers to straight chain hydrocarbon moieties having from 1 to 3 carbon atoms including methyl, ethyl, and n-propyl.

The term "halo" refers to fluoro, chloro, bromo, or iodo. Preferred halo groups are fluoro, chloro, and bromo. More preferred halo groups are fluoro and chloro. DMF means N,N-dimethylformamide. XRPD means X-Ray Powder Diffraction. DSC means Differential Scanning Calorimetry. DCM means dichloromethane. TBME means tert-butyl methyl ether. AKX or AX reagent means Karl Fischer analysis reagent. THF means tetrahydrofuran. HPLC means high performance liquid chromatography. IPA means isopropyl alcohol. RH means Relative Humidity.

The term a "polymorphs of the invention" means the Form A polymorph of the hemisuccinate salt of 2,4,6-trifluoro-N-[6-(1-methyl-piperidine-4-carbonyl)-pyridin-2-yl]-benzamide.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipients and salt must be compatible with the active ingredient of the formulation (e.g. a compound of formula I). It is understood by those of ordinary skill in this art that the terms "pharmaceutical formulation" and "pharmaceutical composition" are generally interchangeable, and they are so used for the purposes of this application.

The term "acid addition salt" refers to a salt of a compound e.g., 2,4,6-trifluoro-N-[6-(1-methyl-piperidine-4-carbonyl)-pyridin-2-yl]-benzamide prepared by reaction of a the free base of the compound with a mineral or organic acid. For exemplification of pharmaceutically acceptable acid addition salts see, e.g., Berge, S. M, Bighley, L. D., and Monkhouse, D. C., *J. Pharm. Sci.*, 66:1, 1977. Compounds which contain an amine functionality are basic in nature and accordingly react with any of a number of inorganic and organic acids to form pharmaceutically acceptable acid addition salts. When a compound is typically an oil at room temperature, it is preferable to convert the free amine to its pharmaceutically acceptable acid addition salts for ease of handling and administration, since the latter are routinely solid at room temperature.

The pharmaceutically acceptable acid addition salts of the invention are typically formed by reacting a compound with an equimolar or excess amount of acid. Alternatively, hemi-salts can be formed by reacting a compound with the desired acid in a 2:1 ratio, compound to acid. The reactants are generally combined in a mutual solvent such as diethylether, tetrahydrofuran, methanol, ethanol, isopropanol, benzene, or the like. The salts normally precipitate out of solution within about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid and succinic acid.

The terms "commercial scale process" and "commercial scale composition" refer to a process and composition, respectively, which is run or produced as a single batch of at least about 100 grams.

The term "effective amount" means an amount of the polymorph of the invention which is capable of activating 5-$HT_{1F}$ receptors and/or inhibiting neuronal protein extravasation.

As used herein, "treating" or "treatment" includes any effect e.g., lessening, reducing, modulating, or eliminating, that results in the improvement of the condition, disease, disorder, etc. "Treating" or "treatment" of a disease state means the treatment of a disease-state in a mammal, particularly in a human, and include: (a) inhibiting an existing disease-state, i.e., arresting its development or its clinical symptoms; and/or (c) relieving the disease-state, i.e., causing regression of the disease state.

As used herein, "preventing" means causing the clinical symptoms of the disease state not to develop i.e., inhibiting the onset of disease, in a subject that may be exposed to or predisposed to the disease state, but does not yet experience or display symptoms of the disease state.

The term "suitable solvent" refers to any solvent, or mixture of solvents, inert to the ongoing reaction that sufficiently solubilizes the reactants to afford a medium within which to effect the desired reaction.

The term "amorphous" as used herein, means essentially without a regularly repeating arrangement of molecules or external face planes.

It is meant to be understood that peak heights in a powder x-ray diffraction pattern may vary and will be dependent on variables such as the temperature, crystal size, crystal habit, sample preparation or sample height in the analysis well.

Figure 3:
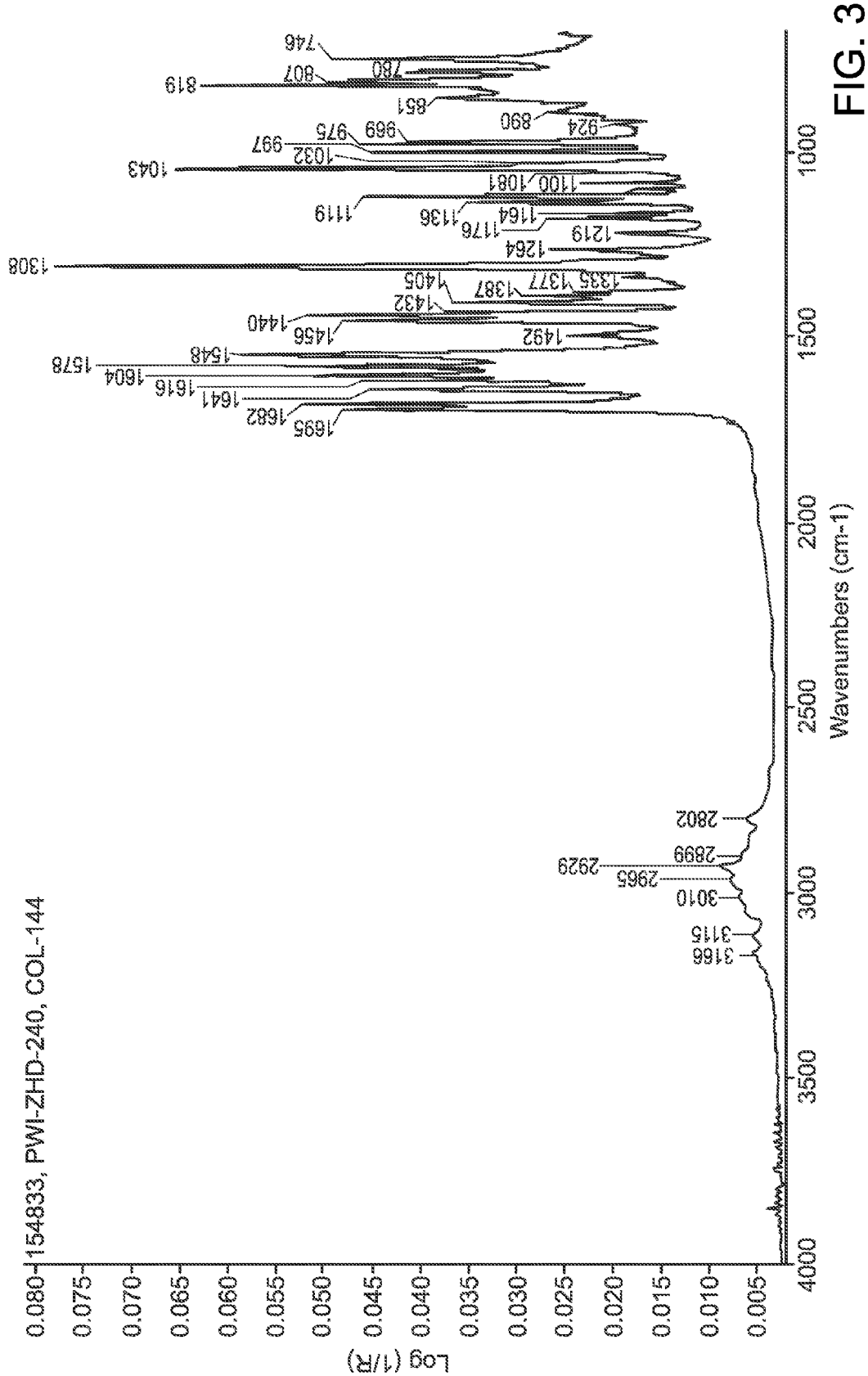
FIG. 3 shows infra-red data for Compound VIII (Form A).

It is meant to be understood that the peak labels in the images in FIGS. 1 and 3 are meant as a visual aid. Consult the corresponding Table for accurate 2θ and cm$^{-1}$ positions.

It is also meant to be understood that peak positions may vary when measured with different radiation sources.

Formulations

The type of formulation used for the administration of the polymorph employed in the methods of the present invention may be dictated by the type of pharmacokinetic profile desired from the route of administration and the state of the patient.

Formulations amenable to oral, sublingual, nasal or injectable administration are prepared in a manner well known in the pharmaceutical art and comprise at least one active compound. See, e.g., REMINGTON'S PHARMACEUTICAL SCIENCES, (16th ed. 1980).

In general, a formulation of the present invention includes an active ingredient (the polymorph of the invention) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, gels, suppositories, sterile injectable solutions, and sterile packaged powders.

In preparing a formulation, it may be necessary to mill the active polymorph to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh. In one embodiment of the present invention, the particle size range is between about 0.1 μm to about 100 μm.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

The following formulation examples are illustrative only and are not intended to limit the scope of the present invention. The term "active ingredient" refers to a polymorph of the invention.

While it is possible to administer a polymorph employed in the methods of this invention directly without any formulation, the polymorph is usually administered in the form of pharmaceutical formulations comprising a pharmaceutically acceptable excipient and at least one active ingredient. These formulations can be administered by a variety of routes including oral, buccal, rectal, intranasal, transdermal, subcutaneous, intravenous, intramuscular, and intranasal. The polymorph employed in the methods of this invention are effective as both injectable and oral compositions.

In order to administer transdermally, a transdermal delivery device ("patch") is needed. Such transdermal patches may be used to provide continuous or discontinuous infusion of a polymorph of the present invention in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intraarterial infusion of hypertonic solutions which can transiently open the blood-brain barrier.

In one embodiment of the present invention, there is provided a pharmaceutical formulation comprising at lest one active polymorph as described above in a formulation adapted for buccal and/or sublingual, or nasal administration. This embodiment provides administration of the active polymorph in a manner that avoids gastric complications, such as first pass metabolism by the gastric system and/or through the liver. This administration route may also reduce adsorption times, providing more rapid onset of therapeutic benefit. The compounds of the present invention may provide particularly favorable solubility profiles to facilitate sublingual/buccal formulations. Such formulations typically require relatively high concentrations of active ingredients to deliver sufficient amounts of active ingredients to the limited surface area of the sublingual/buccal mucosa for the relatively short durations the formulation is in contact with the surface area, to allow the absorption of the active ingredient. Thus, the very high activity of the polymorph of the invention combined with its high solubility, facilitates its suitability for sublingual/buccal formulation.

The invention relates to a pharmaceutical composition comprising an amount of a polymorph of the invention ranging up to 1000 mg per dose administered once, two, or three times daily and a pharmaceutically acceptable diluent or carrier.

The invention relates to a pharmaceutical composition for oral or rectal administration comprising an amount of a polymorph of the invention ranging up to 1000 mg per dose administered once, two or three times daily and a pharmaceutically acceptable diluent or carrier. In one aspect, the invention relates to a pharmaceutical composition comprising an amount of a polymorph of the invention wherein the amount is from 50 mg to 500 mg per dose. In one aspect, the invention relates to a pharmaceutical composition comprising an amount of a polymorph of the invention wherein the amount is from 50 mg to 400 mg per dose. In one aspect, the invention relates to a pharmaceutical composition comprising an amount of a polymorph of the invention wherein the amount is 50 mg per dose. In one aspect, the invention relates to a pharmaceutical composition comprising an amount of a polymorph of the invention wherein the amount is 100 mg per dose. In one aspect, the invention relates to a pharmaceutical composition comprising an amount of a polymorph of the invention wherein the amount is 200 mg per dose. In one aspect, the invention relates to a pharmaceutical composition comprising an amount of a polymorph of the invention wherein the amount is 400 mg per dose.

In one aspect, the invention relates to a pharmaceutical composition comprising a polymorph of the invention or a pharmaceutically acceptable salt, wherein the administration is oral. In one aspect, the invention relates to a pharmaceutical composition comprising an amount of a polymorph of the invention wherein the administration is rectal.

The invention relates to a pharmaceutical composition for buccal, sublingual, nasal/intranasal, transdermal, subcutaneous, injectable, intravenous, or intramuscular administration comprising an amount of a polymorph of the invention ranging up to 200 mg per dose administered once, two or three times daily and a pharmaceutically acceptable diluent or carrier.

In one aspect, the invention relates to a pharmaceutical composition comprising a polymorph of the invention wherein the amount is from 2 to 100 mg per dose. In one aspect, the invention relates to a pharmaceutical composition comprising an amount of a polymorph of the invention wherein the amount is about 10, 15, 25, 30, 45 50, 60, 75, 90 or 100 mg per dose.

In one aspect, the invention relates to a pharmaceutical composition, wherein the administration is buccal. In one aspect, the invention relates to a pharmaceutical composition, wherein the administration is sublingual. In one aspect, the invention relates to a pharmaceutical composition, wherein the administration is nasal or intranasal. In one aspect, the invention relates to a pharmaceutical composition, wherein the administration is transdermal. In one aspect, the invention relates to a pharmaceutical composition, wherein the administration is subcutaneous. In one aspect, the invention relates to a pharmaceutical composition, wherein the administration is injectable. In one aspect, the invention relates to a pharmaceutical composition, wherein the administration is intravenous. In one aspect, the invention relates to a pharmaceutical composition, wherein the administration is intramuscular.

In one aspect, the invention relates to a pharmaceutical composition, wherein the administration of a polymorph of the invention is intravenous. In one aspect, the invention relates to a pharmaceutical composition, wherein the administration of a polymorph of the invention is intravenous over time. In one aspect, the invention relates to a pharmaceutical composition, wherein the administration of a polymorph of the invention is intravenous over a period of about 20 minutes. In one aspect, the invention relates to a pharmaceutical composition, wherein the administration of a polymorph of the invention is intravenous over a period of 20 minutes.

In one aspect, the invention relates to a pharmaceutical composition, wherein the dose of a polymorph of the invention is administered one time daily. In one aspect, the invention relates to a pharmaceutical composition, wherein the dose of a polymorph of the invention is administered two times daily. In one aspect, the invention relates to a pharmaceutical composition, wherein the dose of a polymorph of the invention is administered three times daily.

EXAMPLES

The following Examples are illustrative and should not be interpreted in any way so as to limit the scope of the invention.

Example 1

Synthesis of Title compound 2,4,6-Trifluoro-N-(6-(1-methylpiperidine-4-carbonyl)pyridine-2-yl)benzamide Hemisuccinate VIII (Form A)

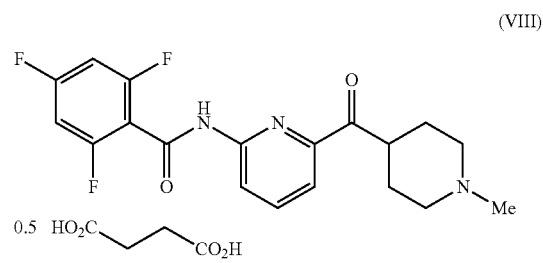

(VIII)

Part A

Charge 2,4,6-Trifluoro-N-(6-(1-methylpiperidine-4-carbonyl)pyridine-2-yl)benzamide Hydrochloride (1.00 wt, 1.00 equiv, 203 g) and TBME (10.0 vol, 7.4 wt, 2.0 L) to the vessel and adjust to the contents to 20 to 25° C. Charge 8% w/w sodium bicarbonate (5.0 vol, 1.0 L) to the vessel maintaining the internal temperature at 20 to 25° C. (caution: evolves CO2) and stir for 60 to 80 minutes at 20 to 25° C. Sample the reaction mixture and check for dissolution (pass criterion: clear, biphasic sample with minimal interfacial solids on standing), sample and analyze the aqueous phase for pH (by stick, pass criterion≥pH8). Separate the phases at 20 to 25° C. and retain the upper (organic) layer. Charge the aqueous layer from previous step to the vessel then charge TBME (10.0 vol, 7.4 wt, 2.0 L) and stir for to 25 minutes at 20 to 25° C. Sample and analyze the aqueous phase for pH (by stick, pass criterion≥pH8). Separate the phases and retain the upper (organic) layer. Charge the combined organic layers to the vessel and concentrate to 10 vol at 25 to 35° C. under reduced pressure. Sample the vessel and analyze for water content by Karl Fischer analysis (AKX reagent, Pass criterion≤2.0% w/w water). Cool to 20 to 25° C. Charge silica gel (0.1 wt, 20.3 g) to the reactor vessel and stir at 20 to 25° C. for at least 30 minutes. Filter the suspension through GF/F and charge the filtrate to a clean reactor vessel. Charge TBME (2.0 vol, 1.4 wt, 406 mL) through the silica gel filter cake and charge to the reactor containing the TBME solution. Concentrate to ca. 4 vol under reduced pressure at 25 to 35° C. Charge ethanol (10.0 vol, 7.9 wt, 2.0 L) and distil to 4 vol under reduced pressure at 25 to 35° C. Charge ethanol (10.0 vol, 7.9 wt, 2.0 L) and distil to 4 vol under reduced pressure at 25 to 35° C. Charge ethanol (10.0 vol, 7.9 wt, 20 L) and distil to 4 vol under reduced pressure at 25 to 35° C. Charge ethanol (10.0 vol, 7.9 wt, 2.0 L) and distil to 4 vol under reduced pressure at 25 to 35° C. Sample the distillation residue and analyze for water content by Karl-Fischer titration (AKX reagent, pass criteria≤0.3% w/w water). Determine the TBME content of the solution by 1H NMR analysis (pass criterion≤0.1% w/w). Transfer the ethanolic solution to a clean tared drum via an in-line filter, followed by a line rinse of ethanol, (0.5 vol, 0.4 wt). Mix thoroughly and sample the ethanol solution for contained weight of 2,4,6-Trifluoro-N-(6-(1-methylpiperidine-4-carbonyl)pyridine-2-yl)benzamide free base. Expected yield: 80 to 100% th, 73 to 91% w/w.

Part B

Inputs from this point are relative to determined content of 2,4,6-Trifluoro-N-(6-(1-methylpiperidine-4-carbonyl)pyridine-2-yl)benzamide freebase Charge the ethanol solution of 2,4,6-Trifluoro-N-(6-(1-methylpiperidine-4-carbonyl)pyridine-2-yl)benzamide free-base (1.00 wt corrected, ca 4.5 vol, 183 g) to a clean reactor via an in-line filter followed by a line rinse of ethanol (0.5 vol, 0.4 wt, 91 mL). Into a second vessel charge succinic acid (0.16 wt, 0.53 equiv, 29.3 g) followed by ethanol (3.0 vol, 2.4 wt, 550 mL) and stir under nitrogen for 40 to 50 minutes at 20 to 25° C., confirm dissolution by visual examination. Heat the contents of the vessel from step 1 to 75 to 80° C. under nitrogen. Charge the solution of succinic acid in ethanol from via an in-line filter into the reactor vessel maintaining 75 to 80° C. followed by a line rinse of ethanol (1.0 vol, 0.8 wt, 183 mL). Cool to 60 to 63° C. visually check the reactor vessel for crystallisation and record the temperature of crystallisation then stir at 60 to 63° C. for 50 to 60 minutes. Cool the reactor vessel contents to 20 to 25° C. over 40 to 60 minutes (approx 1° C./min) and stir at 20 to 25° C. for 4 to 6 hours. Centrifuge the collected solid through 46 micron cloth. Wash the collected solid with clarified ethanol (1.0 vol, 0.8 wt, 183 mL). Dry under vacuum at up to 45° C. until dry by 1H NMR analysis (Pass criterion, ≤0.3% w/w ethanol). Expected yield: 70 to 75% th, 74 to 79% w/w from the input of 2,4,6-trifluoro-N-(6-(1-methylpiperidine-4-carbonyl)pyridine-2-yl)benzamide hydrochloride. Isolated yield: 182 g (85% th, 90% w/w) of the title compound, Form A.

Figure 4:
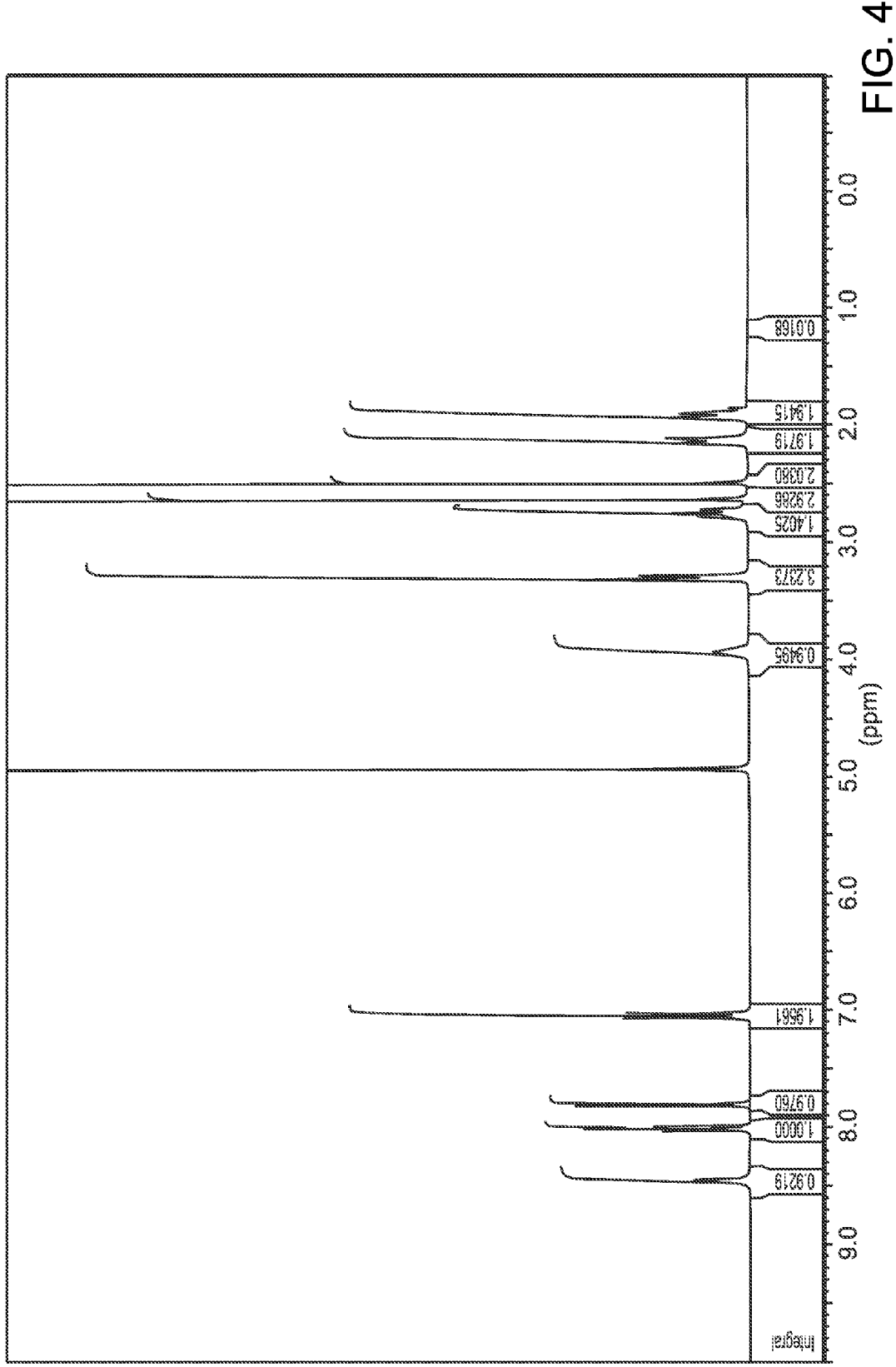
FIG. 4 shows a typical $^1$H NMR spectrum of 2,4,6-trifluoro-N-(6-(1-methylpiperidine-4-carbonyl)pyridine-2-yl)benzamide hemisuccinate, Form A (MeOD).

Form A is a crystalline, non-hygroscopic anhydrate which melts at 198° C. Form A is characterized the X-ray diffraction pattern set forth in FIG. 1A. Further, Form A is also characterized by differential calorimetry (DSC). Form A has an onset of melting transition/decomposition point at about 199°. FIG. 3 shows a typical infrared spectrum of Form A and FIG. 4 shows a typical $^1$HNMR spectrum of Form A(MeOD).

Example 2

Preparations of the intermediates leading up to the title compound 2,4,6-Trifluoro-N-(6-(1-methylpiperidine-4-carbonyl)pyridine-2-yl)benzamide Hemisuccinate (VIII)

Preparations 1. 1-Methylpiperidine-4-carboxylic acid Hydrochloride

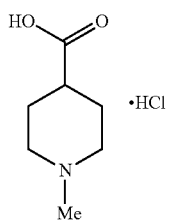

Figure 5:
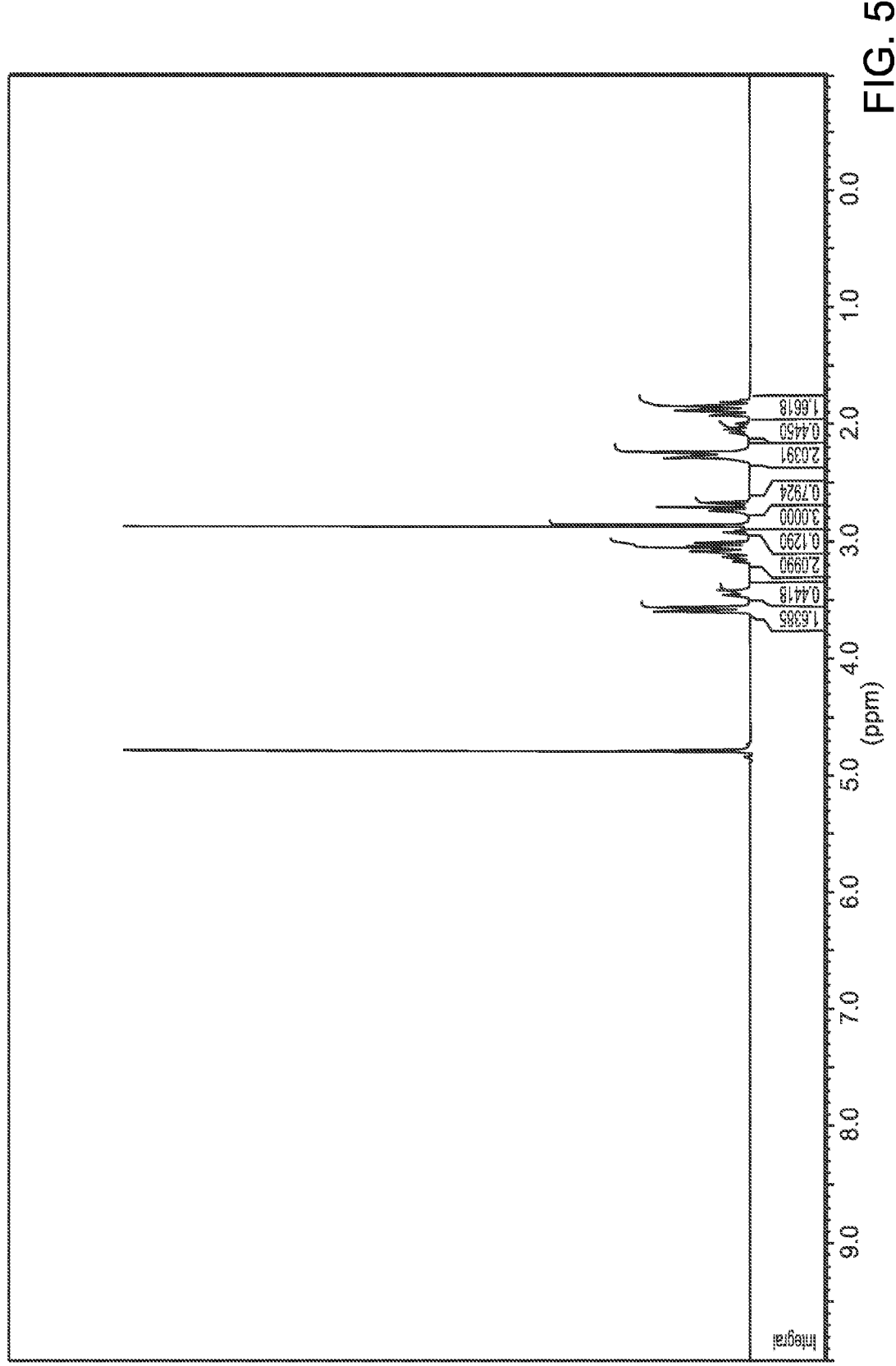
FIG. 5 shows a typical $^1$H NMR spectrum of 1-methylpiperidine-4-carboxylic acid ($D_2O$).

Charge isonipecotic acid (1.00 wt, 1.0 eq, 600 g) to a reaction vessel. Charge palladium on charcoal (10% wt, 50% wet paste, 0.05 wt, 30 g) to the reaction vessel. Charge purified water (4.0 vol, 2.4 L) to the reaction vessel. Heat the resulting mixture to 90 to 95° C. Charge formic acid (1.2 vol, 1.4 wt, 4.0 eq, 720 mL) to the vessel at 90 to 95° C. (expected addition time 20 to 40 minutes). Charge a line rinse of purified water (0.5 vol, 300 mL) to the vessel at 90 to 95° C. Charge formaldehyde (37% w/w aqueous solution, 0.74 vol, 0.81 wt, 1.3 eq, 444 mL) to the vessel at 90 to 95° C. (expected addition time 20 to 40 minutes). Charge a line rinse of purified water (0.5 vol, 300 mL) to the vessel at 90 to 95° C. Stir the resulting mixture at 90 to 100° C. until complete by HPLC analysis (pass criterion≤0.1% area isonipecotic acid, expected 3 hours). Cool the resulting mixture to 20 to 30° C. Filter the reaction mixture through GF/F. Wash the filter cake with purified water (2×1.0 vol) at 20 to 30° C. Concentrate the combined filtrates to ca 2 vol at atmospheric pressure. As necessary adjust the temperature to 65 to 75° C. Charge conc. Hydrochloric acid (0.95 vol, 1.14 wt, 1.5 eq, 570 mL) to the vessel at 65 to 75° C. Charge acetonitrile (10.0 vol, 7.8 wt, 6.0 L) to the vessel at ≥70° C. and concentrate the solution to ca 2 vol at atmospheric pressure. Charge acetonitrile (10.0 vol, 7.8 wt, 6.0 L) to the vessel at ≥70° C. and concentrate the solution to ca 2 vol at atmospheric pressure. Charge acetonitrile (10.0 vol, 7.8 wt, 6.0 L) to the vessel at ≥70° C. and concentrate the solution to ca 3 vol at atmospheric pressure. Check the water content by KF analysis of the supernatant liquors using AX reagent (pass criterion≤0.1% w/w). Cool the reaction mixture to 20 to 25° C. Stir the reaction mixture for 1 to 2 hours at 20 to 25° C. Filter the reaction mixture at 20 to 25° C. Wash the filter cake with acetonitrile (2×1.0 vol, 0.8 wt, 2×600 mL). Dry the product at up to 50° C. until ≤0.5% w/w by LOD and ≤0.2% w/w water (KF, AX reagent). Expected yield: 80 to 90% th, 111 to 125% w/w; Isolated yield: 755 g (91% th, 125 w/w). FIG. 5 shows a typical NMR spectrum of 1-Methylpiperidine-4-carboxylic acid (D2O)

2. N,N-Diethyl-1-methylpiperidine-4-carboxamide

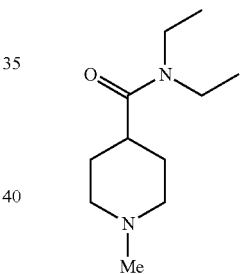

Figure 6:
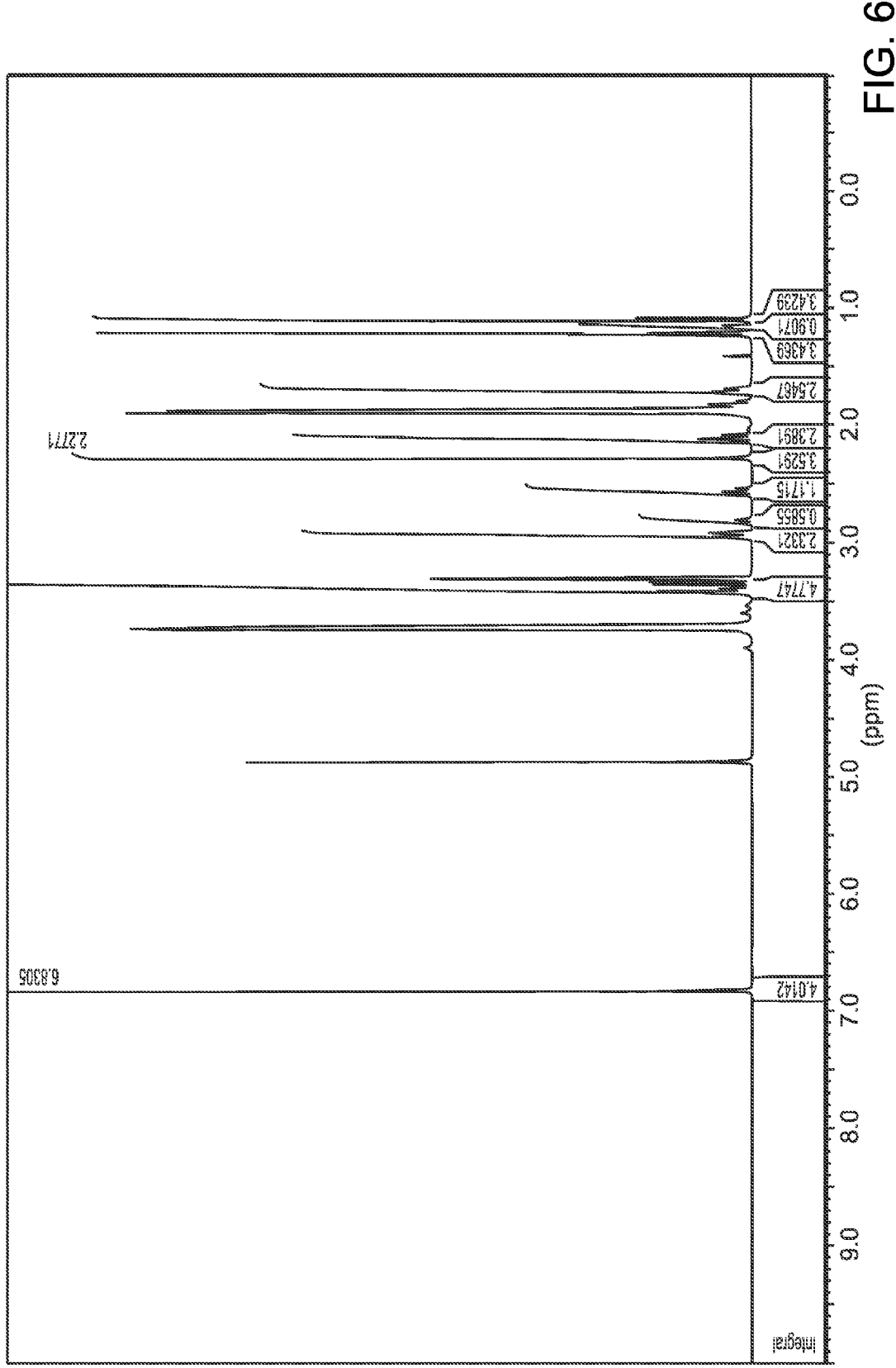
FIG. 6 shows a typical $^1$H NMR spectrum of N,N-diethyl-1-methylpiperidine-4-carboxamide (MeOD).

Charge 1-Methylpiperidine-4-carboxylic acid Hydrochloride (1.00 wt, 1.0 eq, 435 g) to the vessel. Charge THF (10.0 vol, 8.9 wt, 4.4 L) to the vessel. Heat the mixture to 45 to 50° C. Charge thionyl chloride (0.49 vol, 0.79 wt, 1.2 eq, 213 mL) at 45 to 50° C. Charge a line rinse of THF (0.5 vol, 0.4 wt, 218 mL) at 45 to 50° C. Stir the reaction at 45 to 50° C. until complete by GC analysis (pass criterion≤2.0% area 2,4,6-Trifluoro-N-(6-(1-methylpiperidine-4-carbonyl)pyridine-2-yl)benzamide N-methyl acid, completion expected within 5 to 7 hours). Cool the reaction mixture to 0 to 5° C. To a separate vessel charge diethylamine (0.57 wt, 0.81 vol, 1.4 eq, 352 mL), and triethylamine (2.3 vol, 1.7 wt, 3.0 eq, 1.0 L) and mix well. Charge the diethylamine/triethylamine mixture to the reaction mixture at 0 to 10° C. Charge a line rinse of THF (0.5 vol, 0.4 wt, 218 mL) at 0 to 10° C. Stir the reaction mixture at 0 to 10° C. until complete by GC analysis (pass criterion≤2.0% area 2,4,6-Trifluoro-N-(6-(1-methylpiperidine-4-carbonyl)pyridine-2-yl)benzamide N-methyl acid, completion expected within 1 hour). Charge aqueous sodium hydroxide (20% w/v, 10.0 vol, 4.4 L) at 0 to 50° C. Adjust the temperature of the mixture as necessary to 45 to 50° C. and check the pH of the lower aqueous layer using pH stick (pass criterion is pH14). Stir the biphasic mixture for 2 to 3 hours at 45 to 50° C. and check the pH of the lower aqueous layer by pH stick (pass criterion is pH14). Cool the mixture to 20 to 25° C. then separate the layers. Recharge the aqueous layer to the vessel and charge THF (3.0 vol, 2.7 wt, 1.3 L). Stir the mixture at 20 to 25° C. for 15 to 20 minutes then separate the layers. Recharge the aqueous layer from step 0 to the vessel and charge THF (3.0 vol, 2.7 wt, 1.3 L). Stir the mixture at 20 to 25° C. for 15 to 20 minutes then separate the layers. Charge sodium chloride (0.3 wt, 130 g) to the combined organic layers and stir for 20 to 30 minutes at 20 to 25° C. Separate the layers. Clarify the organic layers using GF/F and a 1 µm filter followed by a line rinse of THF (1.5 vol, 1.3 wt, 652 mL) at 20 to 25° C. Concentrate the combined organic filtrates to ca. 3 vol at atmospheric pressure. Charge THF (10.0 vol, 8.9 wt, 4.4 L) and concentrate to ca. 3 vol at atmospheric pressure. Charge THF (10.0 vol, 8.9 wt, 4.4 L) and concentrate to ca. 3 vol at atmospheric pressure. Check the water content of the solution by KF (pass criterion≤0.1% w/w on a filtered sample, AKX reagent). Check the triethylamine content of the solution by 1H NMR (pass criterion≤3% mol triethylamine). Cool the solution to 0 to 5° C. Stir the mixture for 1 to 2 hours at 0 to 5° C. Transfer the solution to a clean tared container via a 1 µm filter. Pass a line rinse of THF (1.0 vol, 0.9 wt, 435 mL) at 0 to 5° C. Determine the yield of the product by performing a w/w assay on the solution in duplicate by 1H NMR (results expected within 1% absolute). Expected yield: 68 to 86% th, 75 to 95% w/w; Isolated yield: 432 g (90% th, 99% w/w). FIG. 6 shows a typical NMR spectrum of N,N-Diethyl-1-methylpiperidine-4-carboxamide (MeOD) (Note: This is of a THF solution during w/w assay determination. The peaks at δ2.3 and 6.8 ppm are due to 1,4 dimethoxybenzene used as an internal standard during yield determination)

3. (6-Bromopyridin-2-yl)(1-methylpiperidin-4-yl) methanone Hydrobromide

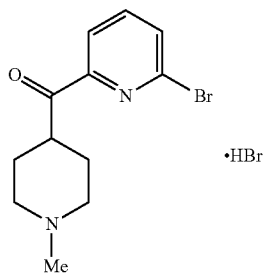 [SMILES: CN1CCC(C(=O)c2cccc(Br)n2)CC1 ; Br]

Figure 7:
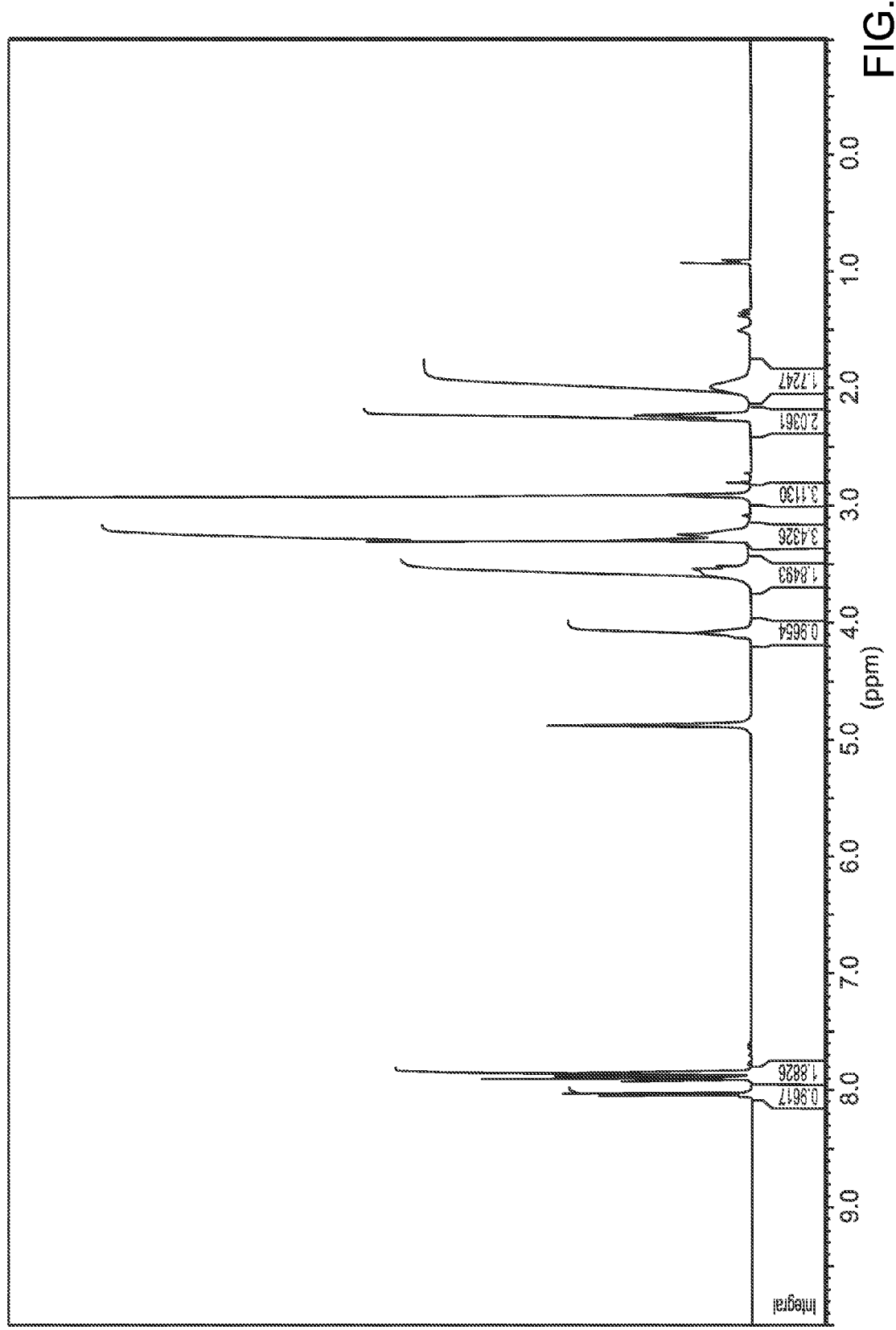
FIG. 7 shows a typical $^1$H NMR spectrum of (6-bromopyridin-2-yl)(1-methylpiperidin-4-yl)methanone hydrobromide (MeOD).

Charge 2,6-dibromopyridine to a reaction vessel (1.67 wt, 1.4 eq, 696 g) followed by THF (7.0 vol, 6.2 wt, 2.9 L) and stir at 18 to 25° C. Charge iPrMgCl/LiCl (Turbo Grignard; ca.14% w/w solution in THF, corrected for assay, 5.7 vol, 1.54 eq, 2.4 L) maintaining the internal temperature at 18 to 25° C. Line rinse with THF (1.0 vol, 0.9 wt, 420 mL). Stir the resulting solution at 18 to 25° C. until complete by 1H NMR analysis. (Pass criterion≥72% mol metallated bromopyridine). Charge N,N-Diethyl-1-methylpiperidine-4-carboxamide THF solution (1.0 wt corrected, ca. 4 vol, 417 g) to the reaction mixture at 18 to 25° C. Line rinse with THF (1.0 vol, 0.9 wt, 420 mL). Stir at 18 to 25° C. until complete by HPLC analysis (pass result≤10% area N-methyl amide). Charge ammonium chloride solution (10% w/v, 6.0 vol, 2.5 L) maintaining the internal temperature at 18 to 25° C. Adjust the pH of the biphasic layer to 7.6 to 7.9 targeting 7.6 to 7.7 with cHCl (ca. 420 mL, ca. 1.0 vol typically required) at 18 to 25° C. and stir for 20 to 40 minutes (target 35 minutes). Check the pH and, if necessary adjust to 7.6 to 7.9. Allow to settle for at least 60 minutes and remove the lower aqueous phase retaining any interfacial material in the aqueous phase. Charge THF (3.0 vol, 2.7 wt, 1.2 L) to the aqueous phase at 18 to 25° C. Check the pH and, if necessary adjust to pH 7.6 to 7.9. Stir for at least 20 minutes and allow to settle for at least 60 minutes then separate the layers retaining any interfacial material in the aqueous phase. Charge THF (3.0 vol, 2.7 wt, 1.2 L) to the aqueous phase at 18 to 25° C. Check the pH and, if necessary adjust to pH 7.6 to 7.9. Stir for at least 20 minutes and allow to settle for at least 60 minutes then separate the layers retaining any interfacial material in the aqueous phase. Charge THF (3.0 vol, 2.7 wt, 1.2 L) to the aqueous phase at 18 to 25° C. Check the pH and, if necessary adjust to pH 7.6 to 7.9. Stir for at least 20 minutes and allow to settle for at least 60 minutes then separate the layers retaining any interfacial material in the organic phase. Charge purified water (6.0 vol, 2.5 L) to the combined organic phases at 18 to 25° C. Charge heptanes (0.5 vol, 0.3 wt, 208 mL) to the mixture at 18 to 25° C. Charge conc HCl acid to the mixture until a pH 1.0 to 1.5 is reached (ca. 1.2 L, expected 0.5 vol) at 18 to 25° C. Separate the layers at 18 to 25° C. Extract the organic layer with 10% v/v cHCl/purified water (3.0 vol, 1.2 L) at 18 to 25° C. Combine the acidic aqueous extracts and charge n-butanol (5.0 vol, 4.1 wt, 2.1 L) at 18 to 25° C. Charge 20% w/v sodium hydroxide solution to adjust the pH to 9.0 to 10.0 (ca. 830 mL, expected ca.2 vol) at 18 to 25° C. Allow to settle for at least 20 minutes and separate the layers at 18 to 25° C. Wash the basic aqueous phase with n-butanol (3.0 vol, 2.4 wt, 1.2 L) at 18 to 25° C. Concentrate the combined organic phases under vacuum at 20 to 30° C. to ca. 6 vol. Charge n-butanol (3.0 vol, 2.4 wt, 1.2 L) and concentrate under vacuum to ca. 6 vol at 20 to 30° C. Determine the water content by KF (AKX reagent; pass criterion≤0.2% w/w). Cool the mixture to 18 to 25° C. and filter at 18 to 25° C. Wash the filter cake with n-butanol (8.0 vol, 6.5 wt, 3.3 L) at 18 to 25° C. Charge 48% w/w aqueous hydrobromic acid solution (0.70 vol, 1.04 wt, 292 mL) to the combined filtrates at up to 30° C. followed by a n-butanol (2.0 vol, 1.6 wt) line rinse. Check the pH of the mixture with a damp pH strip (pass criterion pH≤2). Concentrate to ca. 10 vol by atmospheric distillation (expected temperature 108 to 112° C.). Determine the water content of a filtered sample by KF (AKX reagent, pass criterion≤0.3% w/w water). Cool to 18 to 25° C. and age for 3 to 4 hours. Filter through 100 µm cloth and wash the filter cake with n-butanol (2×1.0 vol, 2×0.8 wt, 2×417 mL) at 18 to 25° C. Dry at up to 50° C. until ≤0.5% w/w n-butanol by 1H NMR. Expected yield: 50 to 80% th, 92 to 148% w/w; Isolated yield: 468 g (61% th, 112% w/w). FIG. 7 shows a typical NMR spectrum of (6-Bromopyridin-2-yl) (1-methylpiperidin-4-yl)methanone Hydrobromide (MeOD).

4. (6-Aminopyridin-2-yl)(1-methylpiperidin-4-yl) methanone Dihydrochloride

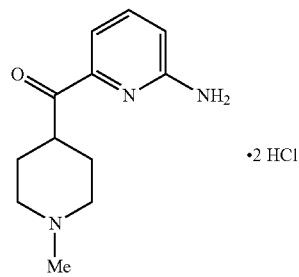 [SMILES: CN1CCC(C(=O)c2cccc(N)n2)CC1 ; "·2 HCl"]

Figure 8:
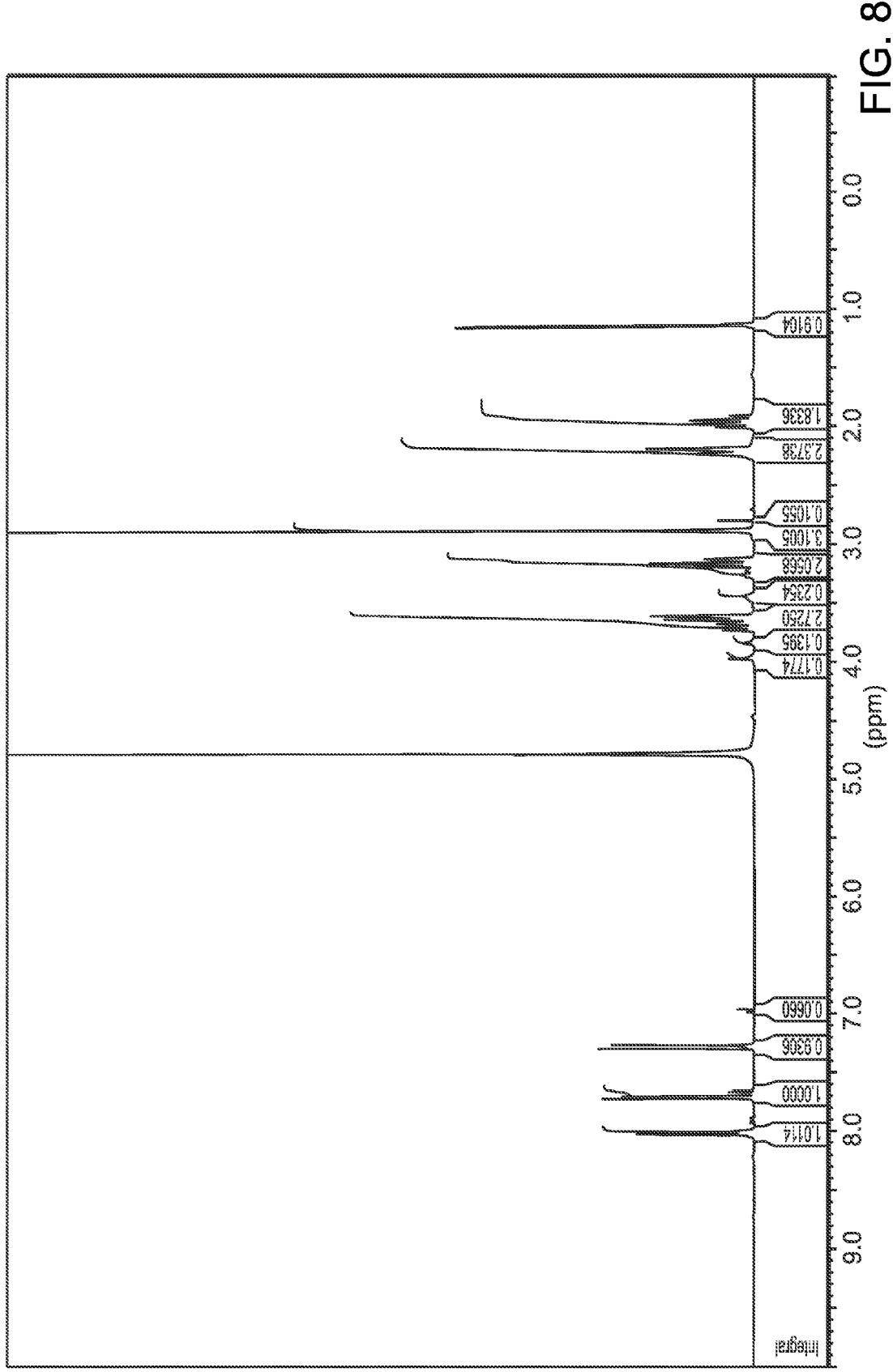
FIG. 8 shows a typical $^1$H NMR spectrum of (6-aminopyridin-2-yl)(1-methylpiperidin-4-yl)methanone dihydrochloride (D2O).

Charge ethylene glycol (8.0 vol, 8.9 wt, 3.3 L) to vessel A and adjust the temperature as necessary to 15 to 25° C. Bubble ammonia gas through vessel A at 15 to 25° C. until a saturated ammonia solution is achieved by titration (pass criterion is ≥14.3% w/w ammonia). To vessel B charge (6-Bromopyridin-2-yl)(1-methylpiperidin-4-yl)methanone Hydrobromide (1.0 wt, 1.0 eq, 414 g). Charge copper(I)oxide (0.05 eq, 0.02 wt, 8.3 g) to vessel B. Transfer the contents of vessel A to vessel B. Seal vessel B and heat the contents to 70 to 75° C. Stir until reaction mixture at 70 to 75° C. at ca 4 to 5 barA until complete by HPLC analysis (pass criterion≤2.0% area starting material, reaction expected to take up to 10 hours). Cool the reaction mixture to 15 to 25° C. Charge aqueous sodium hydroxide (16% w/w, 3.0 vol, 1.2 L) to the vessel at 15 to 25° C. Charge aqueous sodium chloride solution (30% w/w, 20.0 vol, 8.3 L) to the vessel at 15 to 25° C. Charge TBME (5.0 vol, 3.7 wt, 2.1 L) to the vessel at 15 to 25° C. Stir the resulting mixture at 15 to 25° C. for 15 to 30 minutes then separate the layers. Recharge the aqueous layer to the vessel and charge TBME (5.0 vol, 3.7 wt, 2.1 L) at 15 to 25° C. Stir the resulting mixture at 15 to 25° C. for 15 to 30 minutes then separate the layers. Recharge the aqueous layer to the vessel and charge TBME (5.0 vol, 3.7 wt, 21. L) at 15 to 25° C. Stir the resulting mixture at 15 to 25° C. for 15 to 30 minutes then separate the layers. Combine the organic layers and charge activated carbon (0.2 wt) to the vessel. Stir the mixture at 15 to 25° C. for 1 to 2 hours. Filter the reaction mixture (GF/F) at 15 to 25° C. Charge a line rinse of TBME (1.0 vol, 0.7 wt, 414 mL) at 15 to 25° C. Concentrate the combined filtrates to ca 5 vol under vacuum at 20 to 30° C. Charge IPA (10.0 vol, 8.0 wt, 4.1 L) to the vessel and concentrate to ca 5 vol under vacuum at 20 to 30° C. Charge IPA (10.0 vol, 8.0 wt, 4.1 L) to the vessel and concentrate to ca 5 vol under vacuum at 20 to 30° C. Check water content of the solution by KF analysis using AKX reagent (pass criterion≤0.2% w/w). Check the TBME content by 1H NMR analysis (pass criterion≤1.0% w/w relative to 2-propanol, expected ≤0.1% w/w). To separate vessel charge IPA (2.0 vol, 1.6 wt, 830 mL) and cool to 0 to 50° C. Charge acetyl chloride (0.43 wt, 0.39 vol, 178 mL) at ≤25° C. followed by a line rinse of IPA (0.5 vol, 0.4 wt, 207 mL) at ≤25° C. Stir at 20 to 25° C. for 1 to 1.5 hours. Charge the free base solution to acetyl chloride in IPA at step 28 via an in line filter followed by a line rinse with IPA (0.5 vol, 0.4 wt, 207 mL) at 20 to 25° C. Stir at 20 to 25° C. for 2 to 4 hours. Filter the slurry (GF/F) at 20 to 25° C. Wash the filter cake at 20 to 25° C. with IPA (2.0 vol, 1.6 wt, 830 mL). Dry at up to 30° C. until ≤4.4% w/w IPA. Expected yield: 50 to 75% th, 40 to 60% w/w; Isolated yield: 235 g (71% th, 57% w/w). FIG. 8: shows a typical NMR spectrum of (6-Aminopyridin-2-yl)(1-methylpiperidin-4-yl)methanone Dihydrochloride (D2O).

5. 2,4,6-Trifluoro-N-(6-(1-methylpiperidine-4-carbonyl)pyridine-2-yl)benzamide Hydrochloride

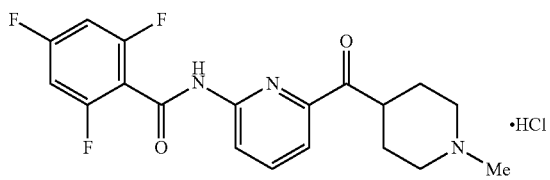 [SMILES: CN1CCC(C(=O)c2cccc(NC(=O)c3c(F)cc(F)cc3F)n2)CC1 ; Cl]

Figure 9:
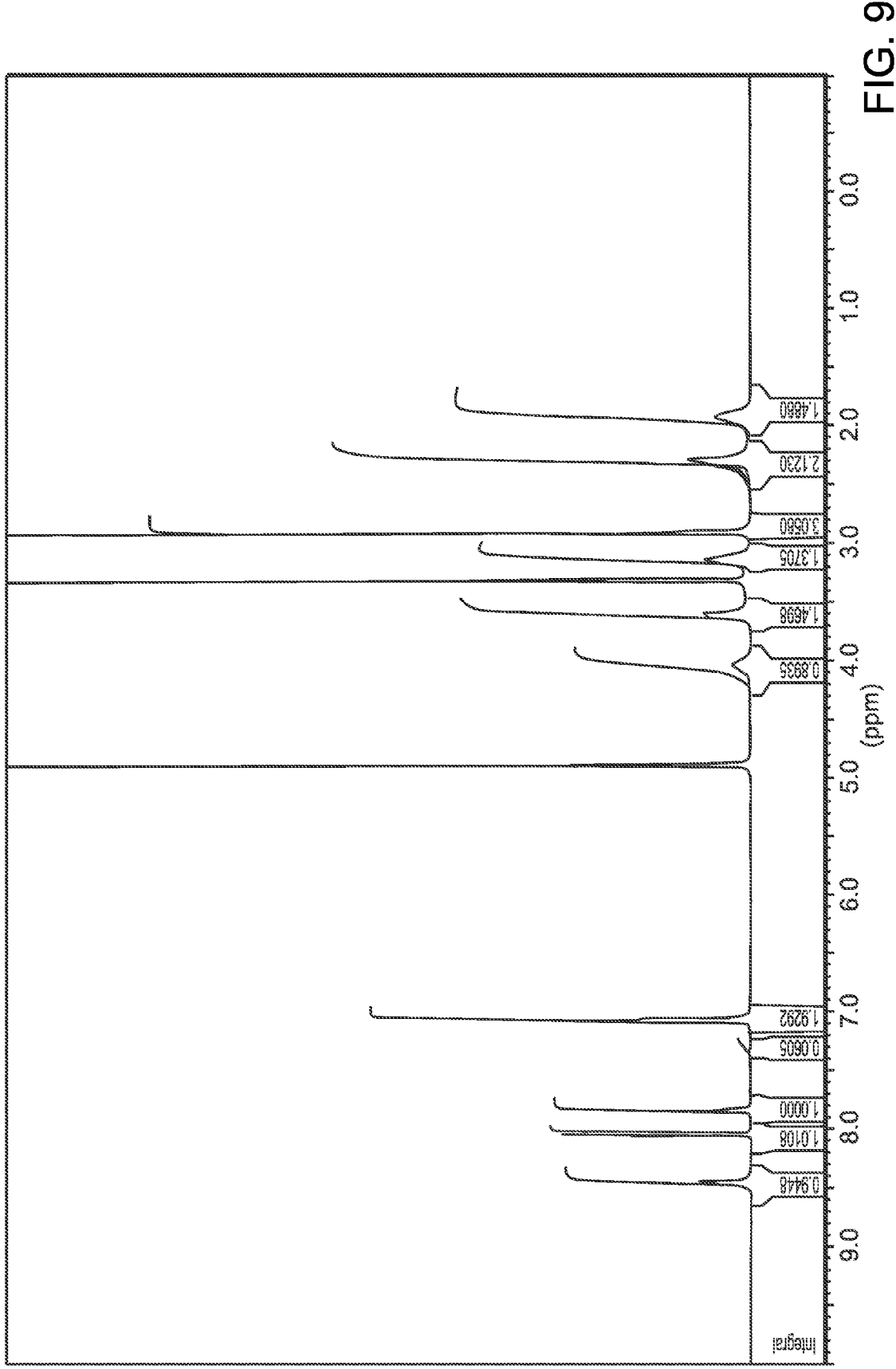
FIG. 9 shows a typical $^1$HNMR spectrum of 2,4,6-trifluoro-N-(6-(1-methylpiperidine-4-carbonyl)pyridine-2-yl)benzamide hydrochloride (MeOD).
Figure 10:
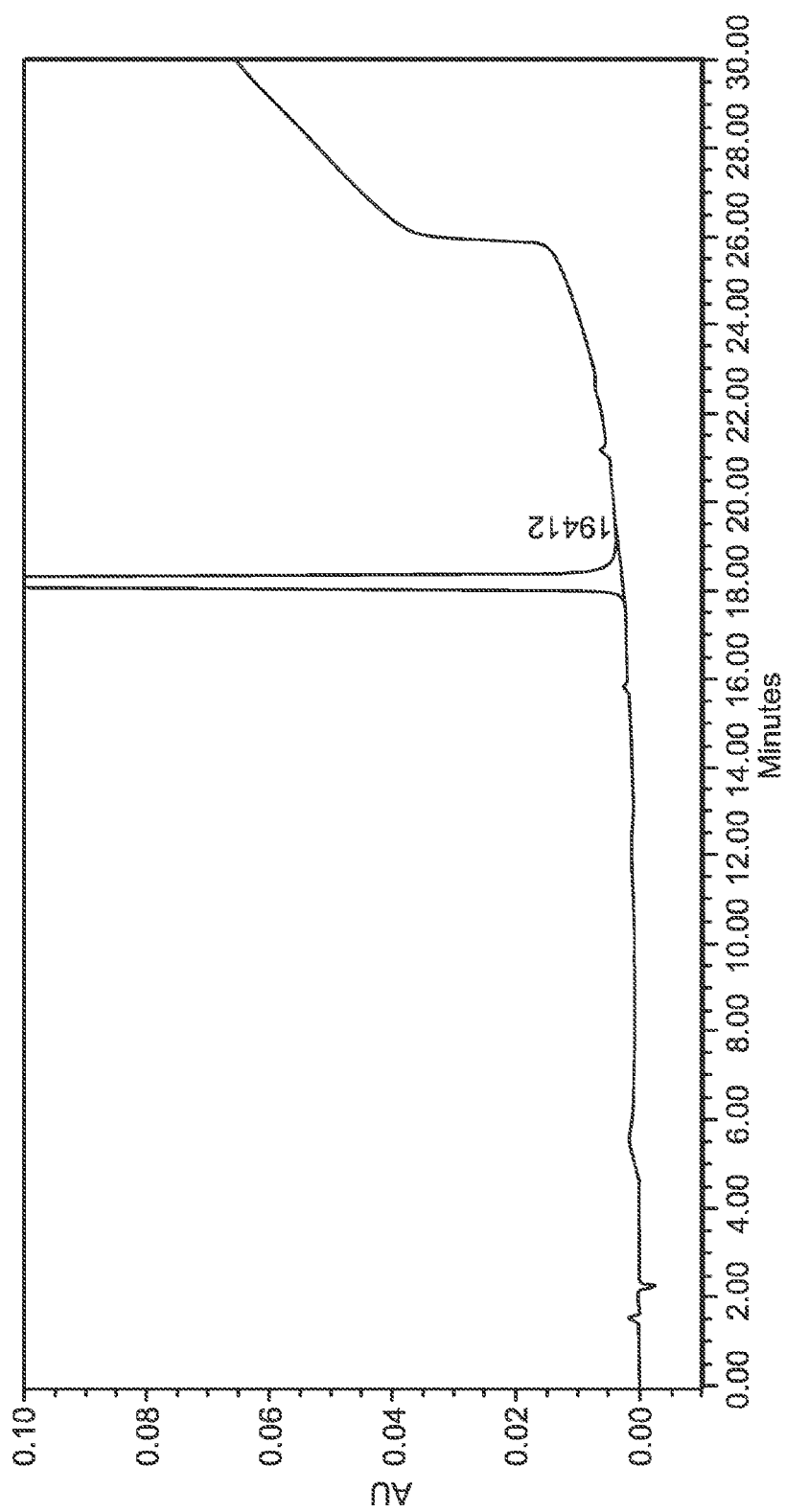
FIG. 10 shows an HPLC trace of 2,4,6-trifluoro-N-(6-(1-methylpiperidine-4-carbonyl)pyridine-2-yl)benzamide having a chemical purity of at least 99% (i.e. main peak normalisation/area % impurities).

Charge (6-Aminopyridin-2-yl)(1-methylpiperidin-4-yl) methanone Dihydrochloride (1.00 wt, 1.00 eq corrected for water and IPA, 194 g) to the vessel. Charge TBME (15.0 vol, 11.1 wt., 2.9 L) and stir at 15 to 25° C. under nitrogen. Charge 8% w/w sodium hydroxide solution (5.0 vol, 970 mL) to the reactor vessel at 15 to 25° C. Stir the resulting biphasic solution for 20 to 25 minutes at 15 to 25° C. Stop the stirring, sample a portion of the aqueous phase and check the pH (pass criterion is pH≥13 by pH stick). Separate the layers. Recharge the lower aqueous layer to the reaction vessel followed by TBME (5.0 vol, 3.7 wt, 970 mL). Stir the resulting biphasic mixture for 20 to 25 minutes at 15 to 25° C. Stop the stirring, sample a portion of the aqueous phase and check the pH (pass criterion pH≥13 by pH stick). Separate the layers. Combine the organic layers and concentrate to ca. 5 vol under vacuum maintaining a temperature of 20 to 30° C. Charge chlorobenzene (6.0 vol, 6.6 wt, 1.2 L) and concentrate to ca. 6 vol under vacuum maintaining a temperature of 25 to 35° C. Charge chlorobenzene (2.0 vol, 2.2 wt, 390 mL) and concentrate to ca. 6 vol under vacuum maintaining a temperature of 25 to 35° C. Check the TBME content by 1H NMR analysis (pass criterion≤1.0% w/w TBME) and the water content by Karl-Fischer titration (pass criterion≤0.1% w/w water, AKX reagent). Charge chlorobenzene (2.0 vol, 2.2 wt, 390 mL) and concentrate to ca. 6 vols under vacuum maintaining a temperature of 25 to 35° C. Check the water content by Karl-Fischer titration, MET/AN/0163 (AKX reagent) for information only. Clarify the solution into a clean tared drum at 30 to 35° C. followed by a chlorobenzene (1.0 vol, 1.1 wt, 194 mL) line rinse at 30 to 35° C. Mix thoroughly and obtain a sample of the mixture for 1H NMR assay analysis for information only. Charge chlorobenzene (4.0 vol, 4.4 wt, 778 mL) to a separate reaction vessel. Charge 2,4,6-trifluorobenzoyl chloride (0.70 wt, 0.46 vol, 1.05 eq, 136 mL). Charge chlorobenzene (1.0 vol, 1.1 wt, 194 mL) as a line rinse. Heat the reaction mixture to 60 to 65° C. Charge the organic solution to the reactor vessel over 30 to 40 minutes maintaining 60 to 65° C. Charge chlorobenzene (1.0 vol, 1.1 wt, 194 mL) to the container and then to the vessel as a line rinse maintaining 60 to 65° C. Heat the resulting suspension to 99 to 101° C. (target 100° C.). Stir the reaction at 98 to 102° C. for 230-250 minutes. Remove a sample for HPLC analysis (pass criterion≤4.3% area, targeting <0.5% area residual (6-Aminopyridin-2-yl)(1-methylpiperidin-4-yl)methanone). Cool the reaction mixture to 15 to 25° C. over 70 to 80 minutes at an approximately constant rate. Filter the suspension through a 46 µm cloth. Wash the filter cake with chlorobenzene (2×2.0 vol, 2×2.2 wt, 2×390 mL) at 15 to 25° C. Dry at up to 45° C. until ≤3000 ppm chlorobenzene by HPLC analysis. Expected yield: 75 to 95% th, 106 to 135% w/w; Isolated yield: 244 g (89% th, 126% w/w). FIG. 9 shows a typical NMR spectrum of 2,4,6-Trifluoro-N-(6-(1-methylpiperidine-4-carbonyl)pyridine-2-yl)benzamide Hydrochloride (MeOD).

Example 3

Preparation of various forms of the title compound 2,4,6-Trifluoro-N-(6-(1-methylpiperidine-4-carbonyl)pyridine-2-yl)benzamide Hemisuccinate (VIII)

In addition to the hemisuccinate salt of 2,4,6-trifluoro-N-[6-(1-methyl-piperidine-4-carbonyl)-pyridin-2-yl]-benzamide (Form A), two other crystalline forms (Form B and Form C) and single crystals of Form A, as well as amorphous samples, were prepared for the studies described in the examples below. The preparation of 2,4,6-trifluoro-N-(6-(1-methylpiperidine-4-carbonyl)pyridine-2-yl)benzamide hemisuccinate (VIII), Form A is described above in Example 1.

Preparation of Single Crystals of Form A
2,4,6-trifluoro-N-(6-(1-methylpiperidine-4-carbonyl)pyridine-2-yl)benzamide hemisuccinate (VIII), Form A (44.7 mg) was combined with ethanol (0.5 mL). The sample was capped and heated on a hotplate to approximately 65° C. with stirring. The resulting clear, slightly yellow solution was filtered using a warm syringe and 0.2 μm nylon filter into a vial containing water (2 mL) which was pre-cooled in an ice-water bath. As no solid material was observed, the sample was placed in the freezer (−25 to −10° C.). After one day, the frozen solution was placed in the refrigerator (2 to 8° C.). A small amount of solid was observed after 57 days and the sample returned to the refrigerator. A clear solution was observed after 47 days and the sample was placed uncapped in the fume hood for solvent evaporation at ambient conditions. Analysis of this crystal is discussed in Example 7.

Preparation of X-ray Amorphous Material 2,4,6-trifluoro-N-(6-(1-methylpiperidine-4-carbonyl)-pyridine-2-yl)benzamide hemisuccinate (VIII), Form A (502.0 mg) was dissolved in 50 mL of water by dispensing aliquots with sonicating after each aliquot addition. The solution was filtered through a 0.2 μm nylon filter into a round-bottom flask. The solution was frozen in a thin layer on the walls of the flask by rotating in a bath of dry ice and washing acetone. The flask was then attached to a Flexi-Dry lyophilizer and covered with aluminum foil to minimize exposure to light. After drying for 2 days, a white solid was obtained with approximately 88% yield, and was analyzed by polarized light microscopy and XRPD. Thermal analysis showed step transitions at 17 and 75° C., possibly due to amorphous succinic acid and free base. A broad exotherm at 155° C. is likely a crystallization. A sharp endotherm at 198° C. is attributed to a melt. Thermogravimetric analysis demonstrated a 1.3% weight loss from 25 to 165° C. FT-IR analysis of amorphous Compound VIII is unique when compared to Form A.

Preparation of Form B 2,4,6-trifluoro-N-(6-(1-methylpiperidine-4-carbonyl)-pyridine-2-yl)benzamide hemisuccinate (VIII), Form A (41.1 mg) was dissolved in 0.7 mL of water with stirring at approximately 55° C., resulting in a clear solution with a light yellow tint. The solution was filtered through a warm 0.2 μm nylon filter (Whatman) into a warm vial. The vial was capped and allowed to cool slowly to room temperature by turning off the hotplate. The vial was sealed with parafilm and wrapped in aluminum foil to minimize exposure to light. A clear solution remained after 3 days of ambient storage. The walls of vial were scratched with a sharp needle to facilitate nucleation. The vial with solution was parafilmed, wrapped in aluminum foil, and placed in the refrigerator at approximately 2° C. Colorless solid crystallized within approximately 3 weeks of storage in the refrigerator. The remaining solution was decanted and the solid air-dried for approximately 1 hour and analyzed.

Preparation of Form C

Amorphous hemisuccinate salt of 2,4,6-trifluoro-N-[6-(1-methyl-piperidine-4-carbonyl)-pyridin-2-yl]-benzamide was stressed at 75% Relative Humidity (RH) and ambient temperature by placing a vial with solid material inside a sealed chamber at the controlled relative humidity conditions. The vial was wrapped in aluminum foil to minimize exposure to light. After 1 day, the resulting dry and dense solid was subsampled and analyzed by polarized light microscopy and XRPD. No changes were noted by visual observation of the sample after 2 and 3 days at 75% RH.

Example 4

X-Ray Powder Diffraction Analysis of the title compound 2,4,6-Trifluoro-N-(6-(1-methylpiperidine-4-carbonyl)pyridine-2-yl)benzamide Hemisuccinate (VIII)

X-Ray Powder Diffraction Analysis was performed on hemisuccinate salt of 2,4,6-trifluoro-N-[6-(1-methyl-piperidine-4-carbonyl)-pyridin-2-yl]-benzamide (Form A), and on two other crystalline forms (Form B and Form C), as well as on amorphous samples.

X-ray powder diffraction analyses were performed using an Inel XRG-3000 X-ray powder diffractometers with Cu K$_\alpha$ radiation. The Inel XRG-3000 diffractometer is equipped with a CPS (Curved Position Sensitive) detector with a 2θ range of 120°. Real time data were collected using Cu—K$_\alpha$ radiation starting at approximately 4° 2θ at a resolution of 0.03° 2θ. The tube voltage and amperage were set to 40 kV and 30 mA, respectively. The monochromator slit was set at 5 mm by 160 μm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 5 min. Instrument calibration was performed using a silicon reference standard.

FIG. 1 depicts X-ray diffraction patterns for various forms of the Compound VIII. FIG. 1A is an X-ray diffraction pattern of Form A, with the data for the observed peaks and representative peaks presented in Tables 1 and 2, respectively.

TABLE 1

Compound VIII Form A

| 2θ | d space (Å) | Intensity (%) |
|---|---|---|
| 7.67±0.10 | 11.524±0.152 | 27 |
| 9.61±0.10 | 9.205±0.097 | 33 |
| 11.06±0.10 | 7.999±0.073 | 21 |
| 13.38±0.10 | 6.618±0.050 | 23 |
| 14.07±0.10 | 6.294±0.045 | 41 |
| 15.11±0.10 | 5.864±0.039 | 51 |
| 15.32±0.10 | 5.785±0.038 | 62 |
| 16.15±0.10 | 5.489±0.034 | 44 |
| 16.39±0.10 | 5.408±0.033 | 100 |
| 16.81±0.10 | 5.276±0.031 | 47 |
| 18.47±0.10 | 4.805±0.026 | 43 |
| 19.33±0.10 | 4.591±0.024 | 61 |
| 21.51±0.10 | 4.130±0.019 | 28 |
| 22.14±0.10 | 4.015±0.018 | 53 |
| 23.18±0.10 | 3.838±0.016 | 46 |
| 23.39±0.10 | 3.804±0.016 | 46 |
| 23.56±0.10 | 3.776±0.016 | 59 |
| 23.84±0.10 | 3.733±0.016 | 33 |
| 24.77±0.10 | 3.594±0.014 | 36 |
| 25.01±0.10 | 3.560±0.014 | 24 |
| 25.91±0.10 | 3.438±0.013 | 52 |
| 26.68±0.10 | 3.342±0.012 | 20 |
| 28.65±0.10 | 3.115±0.011 | 19 |
| 29.31±0.10 | 3.047±0.010 | 12 |

TABLE 2

Compound VIII Form A

| 2θ | d space (Å) | Intensity (%) |
|---|---|---|
| 15.32±0.10 | 5.785±0.038 | 62 |
| 16.39±0.10 | 5.408±0.033 | 100 |
| 19.33±0.10 | 4.591±0.024 | 61 |
| 22.14±0.10 | 4.015±0.018 | 53 |
| 23.56±0.10 | 3.776±0.016 | 59 |
| 25.91±0.10 | 3.438±0.013 | 52 |

Figure 1B:
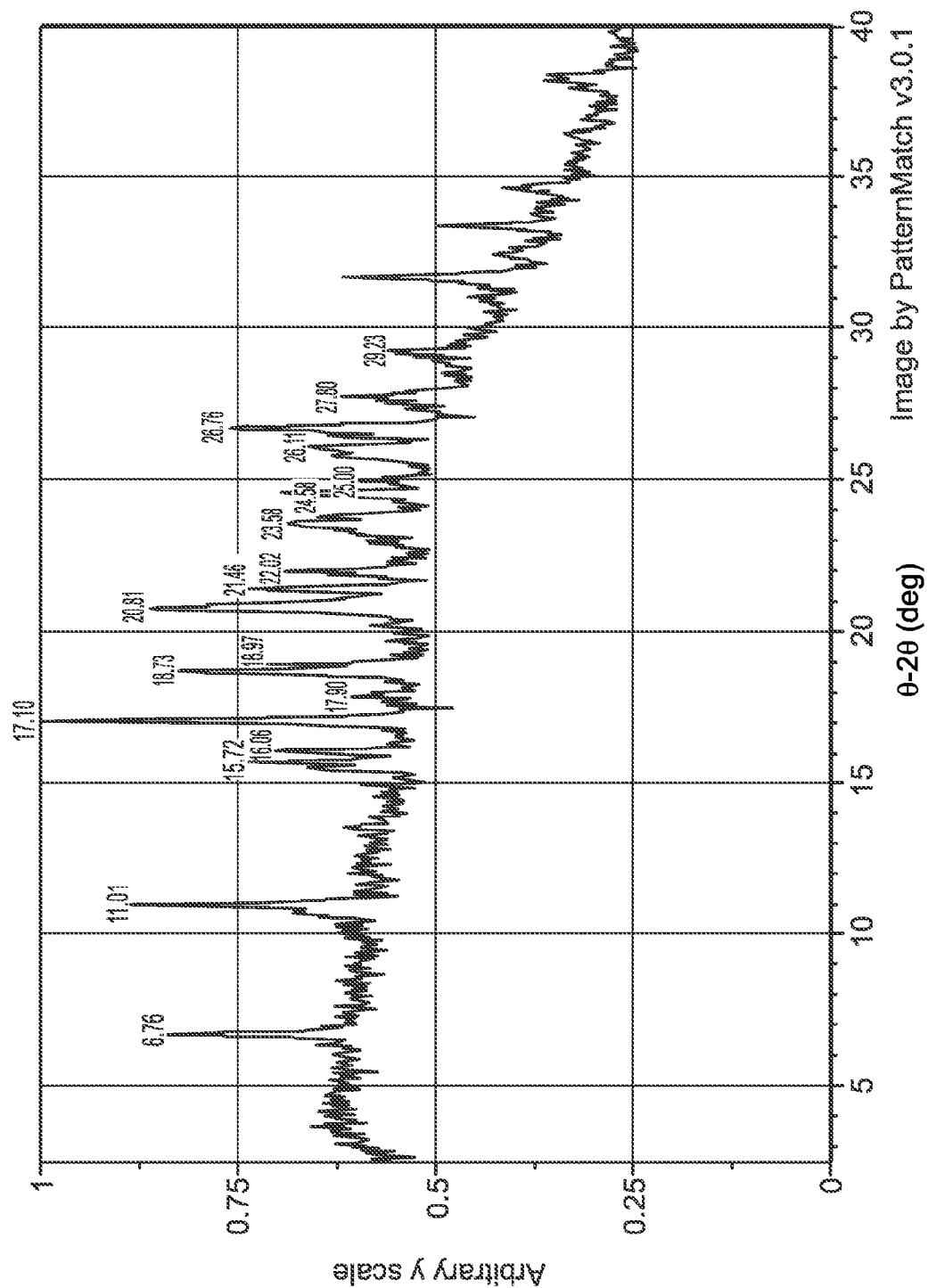
FIG. 1B: Form B.

FIG. 1B is an X-ray diffraction pattern of Form B, with the data for the observed peaks and prominent peaks presented in Tables 3 and 4, respectively.

TABLE 3

Compound VIII Form B

| 2θ | d space (Å) | Intensity (%) |
|---|---|---|
| 6.76±0.10 | 13.080±0.196 | 84 |
| 11.01±0.10 | 8.034±0.073 | 89 |
| 15.72±0.10 | 5.638±0.036 | 73 |
| 16.06±0.10 | 5.517±0.034 | 70 |
| 17.10±0.10 | 5.185±0.030 | 100 |
| 17.90±0.10 | 4.956±0.028 | 60 |
| 18.73±0.10 | 4.738±0.025 | 83 |
| 18.97±0.10 | 4.678±0.025 | 71 |
| 20.81±0.10 | 4.269±0.020 | 86 |
| 21.46±0.10 | 4.140±0.019 | 74 |
| 22.02±0.10 | 4.037±0.018 | 69 |
| 23.58±0.10 | 3.774±0.016 | 69 |
| 24.58±0.10 | 3.622±0.015 | 65 |
| 25.00±0.10 | 3.562±0.014 | 59 |
| 26.11±0.10 | 3.413±0.013 | 64 |
| 26.76±0.10 | 3.331±0.012 | 76 |
| 27.80±0.10 | 3.209±0.011 | 62 |
| 29.22±0.10 | 3.056±0.010 | 53 |

TABLE 4

Compound VIII Form B

| 2θ | d space (Å) | Intensity (%) |
|---|---|---|
| 6.76±0.10 | 13.080±0.196 | 84 |
| 11.01±0.10 | 8.034±0.073 | 89 |
| 17.10±0.10 | 5.185±0.030 | 100 |

Figure 1C:
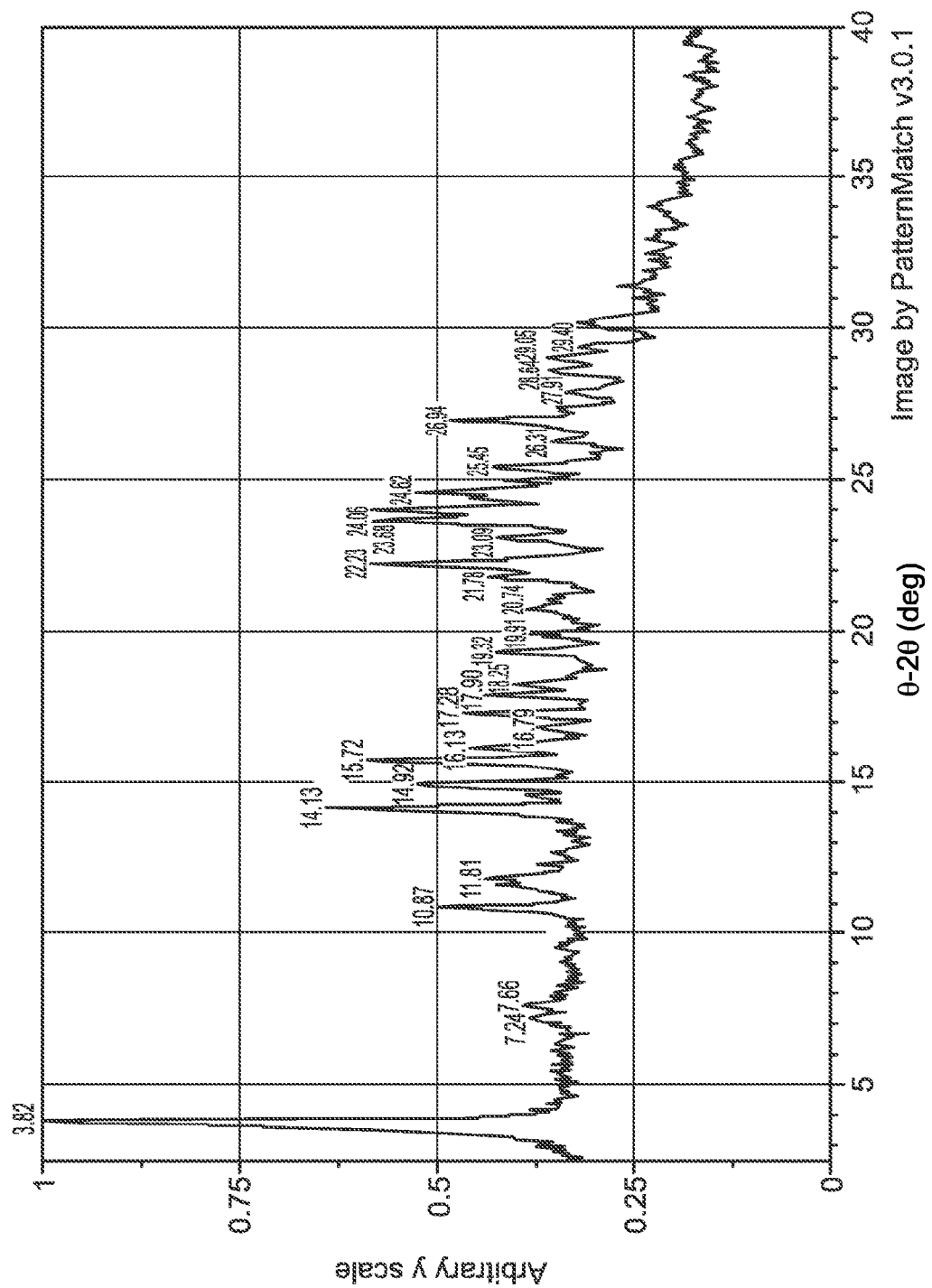
FIG. 1C: Form C.

FIG. 1C is an X-ray diffraction pattern of Form C, with the data for the observed peaks and prominent peaks presented in Tables 5 and 6, respectively.

TABLE 5

Compound VIII Form C

| 2θ | d space (Å) | Intensity (%) |
|---|---|---|
| 3.82±0.10 | 23.141±0.622 | 100 |
| 7.24±0.10 | 12.206±0.171 | 39 |
| 7.66±0.10 | 11.545±0.153 | 39 |
| 10.87±0.10 | 8.136±0.075 | 50 |
| 11.81±0.10 | 7.494±0.064 | 44 |
| 14.13±0.10 | 6.269±0.044 | 64 |
| 14.92±0.10 | 5.937±0.040 | 53 |
| 15.72±0.10 | 5.638±0.036 | 59 |
| 16.13±0.10 | 5.494±0.034 | 46 |
| 16.79±0.10 | 5.280±0.031 | 36 |
| 17.28±0.10 | 5.133±0.030 | 47 |
| 17.90±0.10 | 4.956±0.028 | 44 |
| 18.25±0.10 | 4.863±0.027 | 40 |
| 19.32±0.10 | 4.595±0.024 | 43 |
| 19.91±0.10 | 4.460±0.022 | 39 |
| 20.74±0.10 | 4.283±0.021 | 39 |
| 21.78±0.10 | 4.081±0.019 | 44 |
| 22.23±0.10 | 4.000±0.018 | 59 |
| 23.09±0.10 | 3.852±0.017 | 43 |
| 23.68±0.10 | 3.757±0.016 | 56 |
| 24.06±0.10 | 3.699±0.015 | 57 |
| 24.62±0.10 | 3.617±0.015 | 53 |
| 25.45±0.10 | 3.500±0.014 | 43 |
| 26.31±0.10 | 3.387±0.013 | 36 |
| 26.94±0.10 | 3.310±0.012 | 48 |
| 27.91±0.10 | 3.197±0.011 | 34 |
| 28.64±0.10 | 3.117±0.011 | 36 |
| 29.05±0.10 | 3.074±0.010 | 37 |
| 29.40±0.10 | 3.038±0.010 | 32 |

TABLE 6

Compound VIII Form C

| 2θ | d space (Å) | Intensity (%) |
|---|---|---|
| 3.82±0.10 | 23.141±0.622 | 100 |
| 14.13±0.10 | 6.269±0.044 | 64 |
| 15.72±0.10 | 5.638±0.036 | 59 |
| 22.23±0.10 | 4.000±0.018 | 59 |
| 23.68±0.10 | 3.757±0.016 | 56 |
| 24.06±0.10 | 3.699±0.015 | 57 |

Figure 1D:
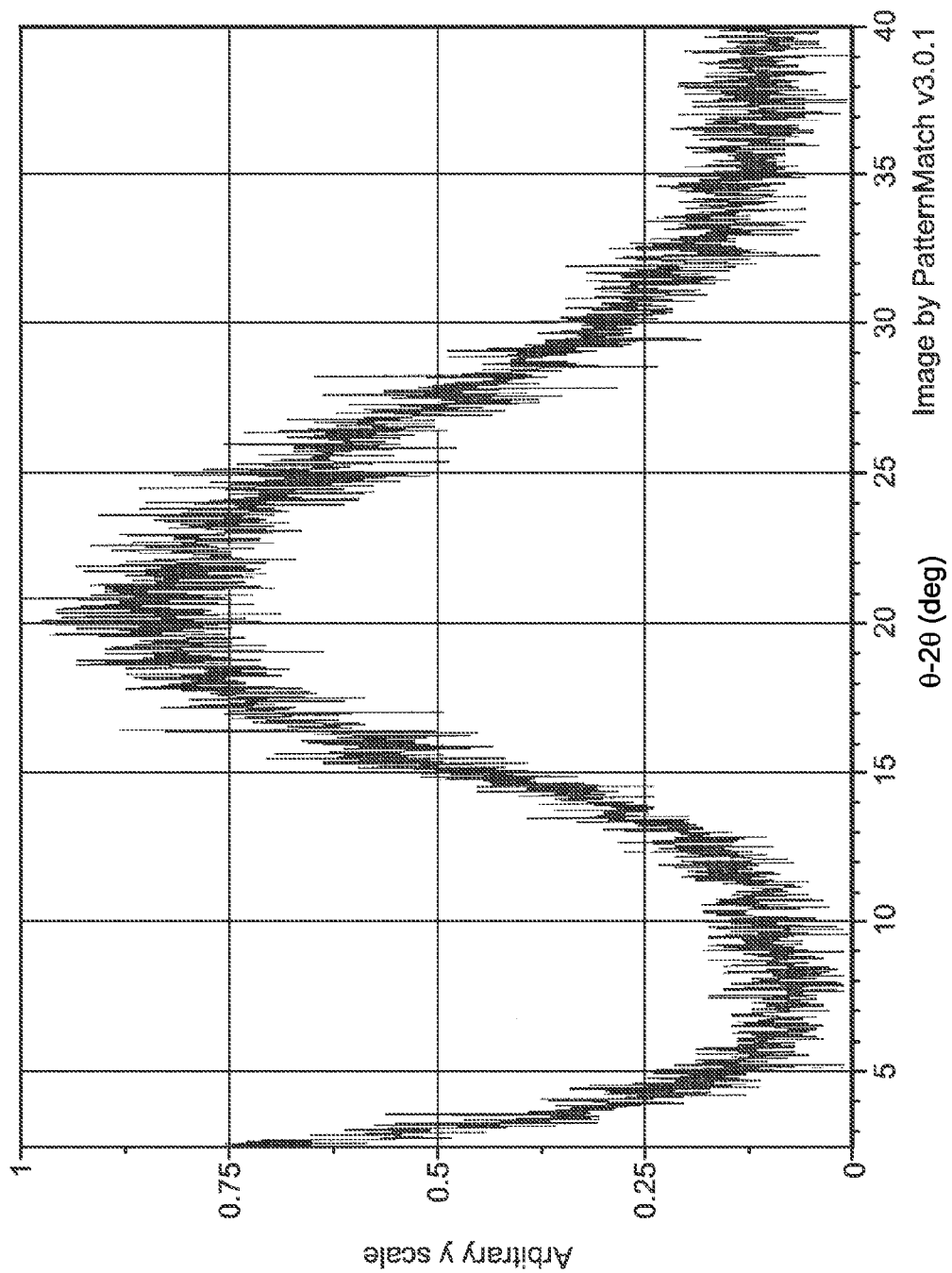
FIG. 1D: amorphous material.

FIG. 1D: amorphous material. FIG. 1D is an X-ray diffraction pattern of a sample of amorphous 2,4,6-Trifluoro-N-(6-(1-methylpiperidine-4-carbonyl)pyridine-2-yl)benzamide Hemisuccinate (VIII).

As evidenced by the data presented above, 2,4,6-trifluoro-N-(6-(1-methylpiperidine-4-carbonyl)pyridine-2-yl)benzamide hemisuccinate (VIII), Form A has a unique XRPD differentiating it from other preparations of the compound.

Example 5

Differential Scanning Calorimetric Analysis of the title compound 2,4,6-Trifluoro-N-(6-(1-methylpiperidine-4-carbonyl)pyridine-2-yl)benzamide Hemisuccinate (VIII)

Differential scanning calorimetry was performed using a TA Instruments differential scanning calorimeter 2920. The sample was placed into an aluminum DSC pan, and the weight accurately recorded. Reported temperatures are at the transition maxima.

Figure 2:
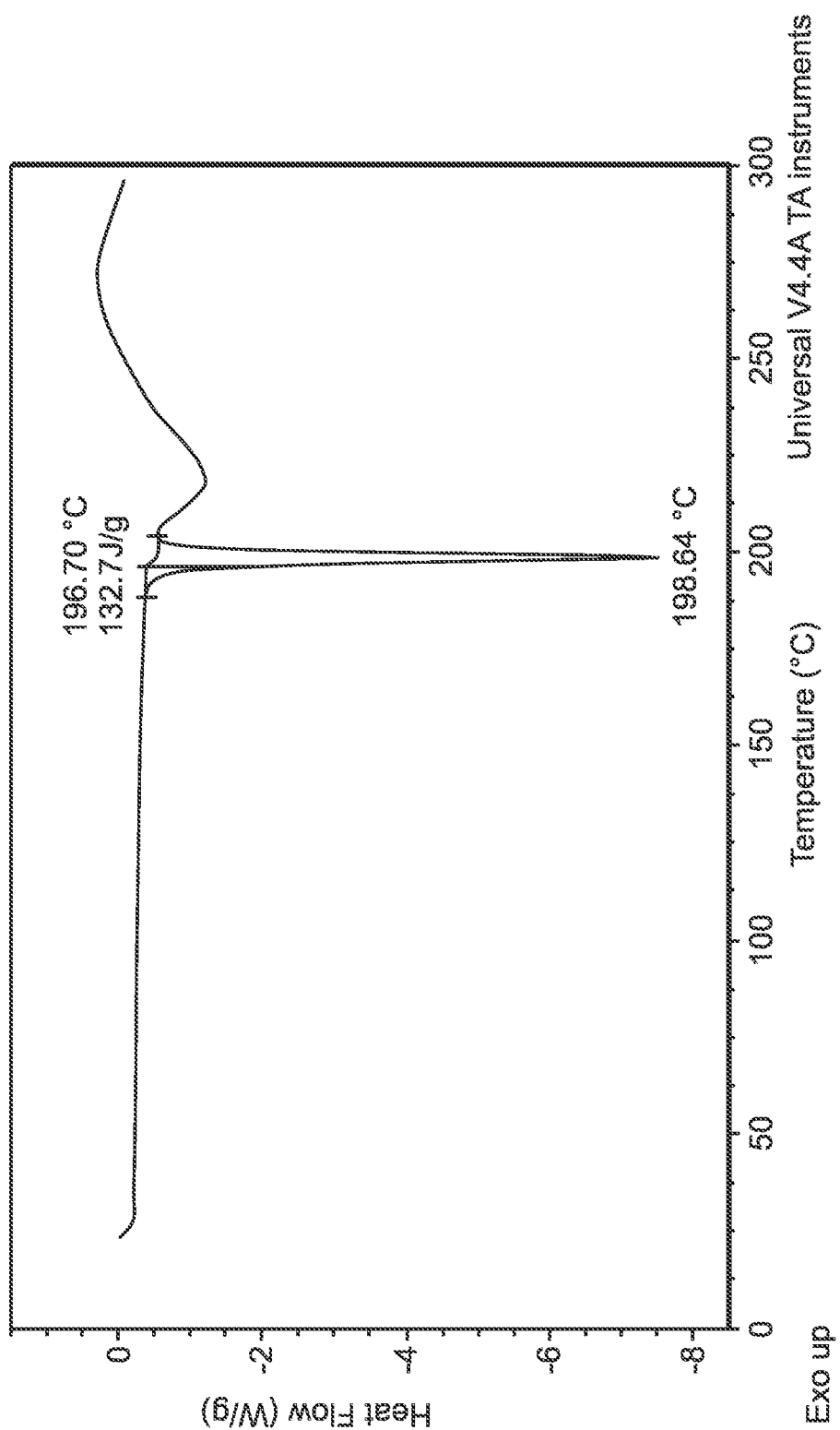
FIG. 2 shows a DSC thermogram of Compound VIII (Form A).

FIG. 2 shows a DSC thermogram of Form A of Compound VIII. The thermogram has a single maximum value at about 199° C. Depending upon the rate of heating, i.e., the scan rate at which the DSC is conducted, the calibration standard used, instrument calibration, the relative humidity and upon the purity, the endotherms may vary. For any given sample, the observed endotherms may also differ from instrument to instrument; however, it will generally be within the ranges defined herein provided the instruments are calibrated similarly.

Example 6

Infrared Analysis of the Title Compound 2,4,6-Trifluoro-N-(6-(1-methylpiperidine-4-carbonyl)pyridine-2-yl)benzamide Hemisuccinate (VIII)

An infrared (IR) spectrum of Compound VIII, Form A was acquired on Magna-IR 860® Fourier transform infrared (FT-IR) spectrophotometer (Thermo Nicolet) equipped with an Ever-Glo mid/far IR source and a deuterated triglycine sulfate (DTGS) detector. An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 cm−1. A background data set was acquired with a clean Ge crystal. Log 1/R(R=reflectance) spectra were acquired by taking a ratio of these two data sets against each other. Wavelength calibration was performed using polystyrene. Observed IR peaks for Compound VIII, Form A are as follows (cm−1): 746, 780, 807, 819, 851, 890, 924, 969, 975, 997, 1032, 1043, 1081, 1100, 1119, 1136, 1164, 1176, 1219, 1264, 1308, 1335, 1377, 1387, 1405, 1432, 1440, 1456, 1492, 1548, 1578, 1604, 1616, 1641, 1682, 1695, 2802, 2899, 2929, 2965, 3010, 3115, 3166.

Example 7

Single Crystal X-Ray Analysis

A single crystal of Compound VIII (Form A) was obtained, as described in Example 3, and investigated by X-ray diffraction. Crystal dimensions were 0.18 mm×0.14 mm×0.10 mm. The crystal was analyzed at 150 Kelvin by X-ray diffraction using Cu—$K_\alpha$ radiation. The crystal was determined to be in the monoclinic space group $P2_1/c$ (No. 14) with unit cell parameters: a=11.8134±0.1 Å, b=14.8302±0.1 Å, c=12.1583±0.1 Å, α=90°, β=104.412±0.3°, and γ angle=90°. The crystal structure was solved. Patterns simulated from the single crystal structure were consistent with the peak positions and intensities of the XRPD patterns for Form A of Compound VIII, indicating adequate particle and orientation statistics for the XRPD patterns for Form A.

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

We claim:

1. A process for preparing 2,4,6-trifluoro-N-[6-(1-methyl-piperidine-4-carbonyl)-pyridin-2-yl]-benzamide or a salt thereof comprising the step of:
   (5) reacting (6-aminopyridin-2-yl)(1-methylpiperidin-4-yl)methanone or a salt thereof with 2,4,6-trifluorobenzoylchloride in the presence of chlorobenzene to yield 2,4,6-trifluoro-N-[6-(1-methyl-piperidin-4-ylcarbonyl)-piperdin-2-yl]benzamide hydrochloride.

2. The process according to claim 1 for preparing 2,4,6-trifluoro-N-[6-(1-methyl-piperidine-4-carbonyl)-pyridin-2-yl]-benzamide or a salt thereof, further comprising the step of:
   (4) reacting (6-bromopyridin-2-yl)(1-methylpiperidin-4-yl)methanone hydrobromide with >0.02 wt % copper(I) oxide at less than 80° C. to yield (6-aminopyridin-2-yl)(1-methylpiperidin-4-yl)methanone.

3. The process according to claim 2 for preparing 2,4,6-trifluoro-N-[6-(1-methyl-piperidine-4-carbonyl)-pyridin-2-yl]-benzamide or a salt thereof, further comprising the step of:
   (3) reacting N,N-diethyl-1-methylpiperidine-4-carboxamide with a solution of 2,6-dibromopyridine and Grignard reagent followed by the addition hydrobromic acid to yield (6-bromopyridin-2-yl)(1-methylpiperidin-4-yl)methanone hydrobromide.

4. The process according to claim 3 for preparing 2,4,6-trifluoro-N-[6-(1-methyl-piperidine-4-carbonyl)-pyridin-2-yl]-benzamide or salt thereof, further comprising the step of:
   (2) reacting 1-methylpiperidine-4-carboxylic acid with thionyl chloride and diethyl amine to yield N,N-diethyl-1-methylpiperidine-4-carboxamide.

5. The process according to claim 4 for preparing 2,4,6-trifluoro-N-[6-(1-methyl-piperidine-4-carbonyl)-pyridin-2-yl]-benzamide or a salt thereof, further comprising the step of:
   (1) converting piperidine-4-carboxylic acid to 1-methylpiperidine-4-carboxylic acid using transfer hydrogenation conditions.

6. The process according to claim 5, for preparing 2,4,6-trifluoro-N-[6-(1-methyl-piperidine-4-carbonyl)-pyridin-2-yl]-benzamide hemisuccinate salt further comprising the step of:
   (6) converting 2,4,6-trifluoro-N-[6-(1-methyl-piperidin-4-ylcarbonyl)-piperdin-2-yl]benzamide hydrochloride using succinic acid in the presence of ethanol to yield 2,4,6-trifluoro-N-[6-(1-methyl-piperidin-4-ylcarbonyl)-piperdin-2-yl]benzamide hemi-succinate salt.

7. A process for preparing a compound of formula I:

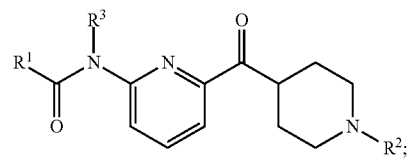

or pharmaceutically acceptable acid addition salts thereof, where;
$R^1$ is phenyl substituted with one to three halo substituents;
$R^2$ is $C_1$-$C_3$ alkyl; and
$R^3$ is hydrogen or $C_1$-$C_3$ alkyl, comprising the steps of:
   (1) converting piperidine-4-carboxylic acid to a compound of formula IA:

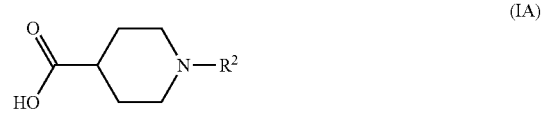

using acid using transfer hydrogenation conditions;
   (2) reacting a compound of formula IA with thionyl chloride and diethyl amine to yield a compound of formula IB:

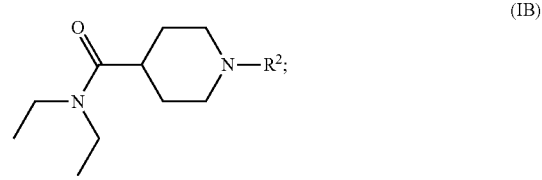

(3) reacting a compound of formula IC with a solution of 2,6-dibromopyridine and Grignard reagent followed by treatment with hydrobromic acid to the salt of formula IC:

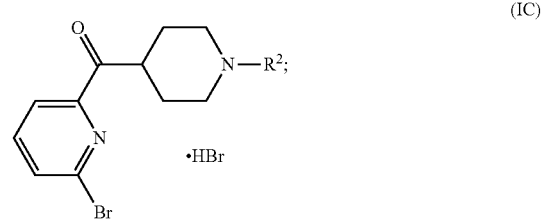

(4) reacting a salt of formula IC with >0.02 wt % copper (I)oxide at less than 80° C. to yield a compound of formula ID:

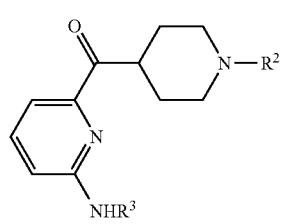 (ID)
and
(5) reacting a compound of formula ID with 2,4,6-trifluorobenzoylchloride in the presence of chlorobenzene to yield a compound of formula I.
* * * * *